(12) United States Patent
Izawa et al.

(10) Patent No.: US 11,266,753 B2
(45) Date of Patent: Mar. 8, 2022

(54) 2-[5-(IMIDAZOL-1-YLMETHYL) PYRIDIN-3-YL]BENZIMTDAZOLE DERIVATIVE COMPOUND, AND MEDICAMENT INCLUDING SAME

(71) Applicants: Nihon Medi-Physics Co., Ltd., Tokyo (JP); National Hospital Organization, Tokyo (JP)

(72) Inventors: Akihiro Izawa, Tokyo (JP); Yuki Okumura, Tokyo (JP); Yurie Fukui, Tokyo (JP); Hiroaki Ichikawa, Tokyo (JP); Yoshifumi Maya, Tokyo (JP); Miho Ikenaga, Tokyo (JP); Hiroyuki Okudaira, Tokyo (JP); Yoshihiro Doi, Tokyo (JP); Mitsuhide Naruse, Kyoto (JP)

(73) Assignees: NIHON MEDI-PHYSICS CO., LTD., Tokyo (JP); NATIONAL HOSPITAL ORGANIZATION, Tokyo (JP)

( * ) Notice: Subject to any disclaimer, the term of this patent is extended or adjusted under 35 U.S.C. 154(b) by 0 days.

(21) Appl. No.: 16/958,427

(22) PCT Filed: Dec. 20, 2018

(86) PCT No.: PCT/JP2018/047092
§ 371 (c)(1),
(2) Date: Jun. 26, 2020

(87) PCT Pub. No.: WO2019/131458
PCT Pub. Date: Jul. 4, 2019

(65) Prior Publication Data
US 2021/0060186 A1 Mar. 4, 2021

(30) Foreign Application Priority Data
Dec. 28, 2017 (JP) .............................. JP2017-253837

(51) Int. Cl.
| | | |
|---|---|---|
| A61K 51/00 | (2006.01) | |
| A61M 36/14 | (2006.01) | |
| A61K 51/04 | (2006.01) | |
| C07B 59/00 | (2006.01) | |
| C07D 401/14 | (2006.01) | |

(52) U.S. Cl.
CPC ........ A61K 51/0455 (2013.01); C07B 59/002 (2013.01); C07D 401/14 (2013.01)

(58) Field of Classification Search
CPC . A61K 51/0455; C07B 59/002; C07D 401/14
USPC ...................................................... 424/1.89
See application file for complete search history.

(56) References Cited

U.S. PATENT DOCUMENTS

| | | |
|---|---|---|
| 2017/0158668 A1 | 6/2017 | Izawa et al. |
| 2019/0255199 A1 | 8/2019 | Maya |

FOREIGN PATENT DOCUMENTS

| | | | |
|---|---|---|---|
| CA | 2953692 A1 * | 12/2015 | ......... A61K 31/4439 |
| WO | 2007144725 A2 | 12/2007 | |
| WO | 2011151411 A1 | 12/2011 | |
| WO | 2012012478 A1 | 1/2012 | |
| WO | 2015199205 A1 | 12/2015 | |
| WO | 2017213247 A1 | 12/2017 | |

OTHER PUBLICATIONS

Amar, et al., "Aldosterone Synthase Inhibition With LCI699—A Proof-of-Concept Study in Patients With Primary Aldosteronism", Hypertension, Nov. 2010, vol. 56, pp. 831 to 838.
De Jong, et al., "Etomidate Suppresses Adrenocortical Function by Inhibition of 11β-Hydroxylation", Journal of Clinical Endocrinology & Metabolism, 1984 (month unknown), vol. 59, No. 6, pp. 1143 to 1147.
Forman, et al., "Clinical and Molecular Pharmacology of Etomidate", Anesthesiology, Sep. 2011, vol. 114, No. 3, pp. 695 to 707.
Hahner, et al., "[$^{123}$I]Iodometomidate for Molecular Imaging of Adrenocortical Cytochrome P450 Family 11B Enzymes", Journal of Clinical Endocrinology & Metabolism, Jun. 2008, vol. 93, No. 6, pp. 2358 to 2365.
Hahner, et al., "Functional Characterization of Adrenal Lesions Using [$^{123}$I]IMTO-SPECT/CT", Journal of Clinical Endocrinology & Metabolism, Apr. 2013, vol. 98, No. 4, pp. 1508 to 1518.
International Search Report (PCT/ISA/210) and an English translation thereof, and Written Opinion (PCT/ISA/237) dated Mar. 19, 2019, by the Japanese Patent Office as the International Searching Authority for International Application No. PCT/JP2018/047092.
Burton, et al. "Evaluation of the Sensitivity and Specificity of $^{11}$C-Metomidate Positron Emission Tomography (PET)-CT for Lateralizing Aldosterone Secretion by Conn's Adenomas" Journal of Clinical Endocrinology & Metabolism, Jan. 2012, vol. 97, No. 1, pp. 1-10.
Nanba et al., "Histopathological Diagnosis of Primary Aldosteronism Using CYP11B2 Immunohistochemistry", Journal of Clinical Endocrinology & Metabolism, Apr. 2013, vol. 98, No. 4, pp. 1567 to 1574.

(Continued)

*Primary Examiner* — Michael G. Hartley
*Assistant Examiner* — Sean R Donohue
(74) *Attorney, Agent, or Firm* — Buchanan Ingersoll & Rooney PC

(57) ABSTRACT

Provided are a compound represented by the following formula (1):

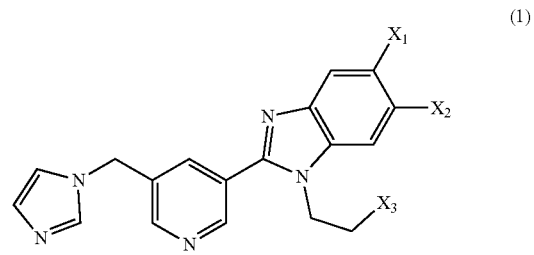

wherein $X_1$ represents a hydrogen atom or a halogen atom, $X_2$ represents a fluorine atom or a nitrile group, and $X_3$ represents a radioactive halogen atom,
or a salt thereof, and a medicament including the same.

9 Claims, 3 Drawing Sheets

(56) References Cited

OTHER PUBLICATIONS

Wadsak, et al., "[$^{18}$F]FETO for adrenocortical PET imaging: a pilot study in healthy volunteers", European Journal of Nuclear Medicine and Molecular Imaging, Jun. 2006, vol. 33, No. 6, pp. 669 to 672.
Zetting, et al., "Positron emission tomography imaging of adrenal masses: $^{18}$F-fluorodeoxyglucose and the 11β-hydroxylase tracer $^{11}$C-metomidate", European Journal of Nuclear Medicine and Molecular Imaging, Sep. 2004, vol. 31, No. 9, pp. 1224 to 1230.
International Preliminary Report on Patentability dated Jun. 30, 2020, by the International Bureau of WIPO in corresponding International Patent Application No. PCT/JP2018/047092. (5 pages).
Extended European Search Report dated Jan. 18, 2021, by the European Patent Office in corresponding European Patent Application No. 18895172.7. (8 pages).

\* cited by examiner

| SAMPLE | IMMUNOHISTOCHEMICAL STAINING | COMPOUND [¹⁸F] 100 (CONTROL) | COMPOUND [¹⁸F] 101 | COMPOUND [¹⁸F] 102 | COMPOUND [¹⁸F] 103 |
|---|---|---|---|---|---|
| 1 |  |  |  |  |  |
| 2 |  |  |  |  |  |
| 3 |  |  |  |  |  |
| 4 |  |  |  |  |  |
| 5 |  |  |  |  |  |
| 6 |  |  |  |  |  |

2-[5-(IMIDAZOL-1-YLMETHYL) PYRIDIN-3-YL]BENZIMTDAZOLE DERIVATIVE COMPOUND, AND MEDICAMENT INCLUDING SAME

TECHNICAL FIELD

The present invention relates to a 2-[5-(imidazol-1-ylmethyl)pyridin-3-yl]benzimidazole derivative compound, and a medicament including the same.

BACKGROUND ART

As a disease developed as a result of abnormality in adrenal cortex, primary aldosteronism (PA) has been known. Primary aldosteronism is a disease in which aldosterone synthase (CYP11B2) is overexpressed by adrenal adenoma or adrenal hyperplasia (Non Patent Literature 1), and autonomous production of aldosterone from adrenal gland is promoted, thereby causing hypertension or hypokalemia. In the case of unilateral adrenal lesion, it can be treated by surgical excision. However, in the case of bilateral adrenal lesion, a treatment with drug therapy is adopted.

As a drug therapy performed on primary aldosteronism, an aldosterone receptor antagonist is mainly used at present. As another target molecule in drug therapy, an aldosterone synthase, CYP11B2, has been considered (Non Patent Literature 2).

Etomidate has been used as an intravenous anesthetic in another country than Japan, and has been known to mainly bind to 11β hydroxylase (CYP11B1) required for biosynthesis of cortisol, corticosterone and aldosterone, and inhibit it, thereby suppressing steroid synthesis in adrenal cortex (Non Patent Literature 3). Thus, it has been reported that etomidate has such side effects that it causes reductions in concentrations of aldosterone and cortisol in plasma (Non Patent Literature 4).

In addition, in recent years, aiming for non-invasive local diagnosis of aldosterone-producing adenoma and other adrenal lesions, an attempt of imaging adrenal lesions by single-photon emission computed tomography (SPECT) or positron emission tomography (PET) has been made in humans. Patent Literatures 1 and 2 and Non Patent Literatures 5 to 8 have reported various types of radiolabeled compounds targeting adrenal steroid biosynthetic enzymes. For example, results of clinical studies are disclosed on $^{11}$C-labeled metomidate in Non Patent Literatures 5 and 8, on $^{18}$F-labeled etomidate in Non Patent Literature 6, and on $^{123}$I-labeled iodometomidate in Non Patent Literatures 7 and 9. It has been reported that adrenal lesions can be imaged using these radiolabeled compounds.

The present inventors have found that a 2-(3-pyridinyl)-1H-benzimidazole derivative compound specifically accumulates in an aldosterone-producing tumor, and have already proposed that the compound is used as a diagnostic imaging agent for an adrenal gland disease, a therapeutic agent for an aldosterone-producing tumor, or the like (Patent Literature 4).

CITATION LIST

Patent Literature

Patent Literature 1: International Publication No. WO 2007/144725
Patent Literature 2: International Publication No. WO 2011/151411
Patent Literature 3: International Publication No. WO 2012/012478
Patent Literature 4: International Publication No. WO 2015/199205

Non Patent Literature

Non Patent Literature 1: Kazutaka Nanba et al., Journal of Clinical Endocrinology & Metabolism (2013) Vol. 98, No. 4, pp. 1567 to 74
Non Patent Literature 2: Amar, et al., Hypertension, (2010) Vol. 56, pp. 831 to 8
Non Patent Literature 3: de Jong et al., Journal of Clinical Endocrinology & Metabolism (1984) Vol. 59, No. 6, pp. 1143 to 7
Non Patent Literature 4: Forman et al., Anesthesiology (2011) Vol. 114, No. 3, pp. 695 to 707
Non Patent Literature 5: Georg Zettinig, et al., European Journal of Nuclear Medicine and Molecular Imaging (2004) Vol. 31, No. 9, pp. 1224 to 1230
Non Patent Literature 6: Wolfgang Wadsak, et al., European Journal of Nuclear Medicine and Molecular Imaging (2006) Vol. 33, No. 6, pp. 669 to 672
Non Patent Literature 7: Stefanie Hahner, et al., Journal of Clinical Endocrinology & Metabolism (2008) Vol. 93, No. 6, pp. 2358 to 2365
Non Patent Literature 8: Timothy J. Burton, et al., Journal of Clinical Endocrinology & Metabolism (2012) Vol. 97, No. 1, pp. 100 to 109
Non Patent Literature 9: Stefanie Hahner, et al., Journal of Clinical Endocrinology & Metabolism (2013) Vol. 98, No. 4, pp. 1508 to 18

SUMMARY OF INVENTION

In Patent Literature 3, a compound that is highly selective for CYP11B2 has been disclosed, but the specific accumulation in an aldosterone-producing tumor relative to a normal site of the adrenal gland has not been indicated at all.

Further, in Patent Literature 4, a given specific binding ability of a 2-(3-pyridinyl)-1H-benzimidazole derivative compound to a human aldosterone-producing tumor has been disclosed, but a compound having a higher binding ability to the human aldosterone-producing tumor has been demanded.

The present invention has been made in view of such circumstances as above, and an object of the present invention is to provide a compound having specific and higher binding ability to an aldosterone-producing tumor, and a medicament including the same.

That is, one aspect of the present invention is to provide a compound represented by the following formula (1) or a salt thereof.

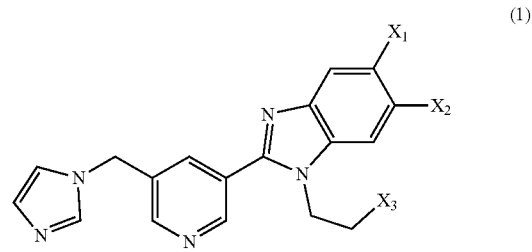

In the above formula (1), $X_1$ represents a hydrogen atom or a halogen atom, $X_2$ represents a fluorine atom or a nitrile group, and $X_3$ represents a radioactive halogen atom. In a case where $X_1$ is a hydrogen atom, $X_2$ is preferably a fluorine atom. In a case where $X_1$ is a halogen atom, $X_2$ may be either a fluorine atom or a nitrile group.

Another aspect of the present invention is to provide a compound represented by the following formula (2) or a salt thereof.

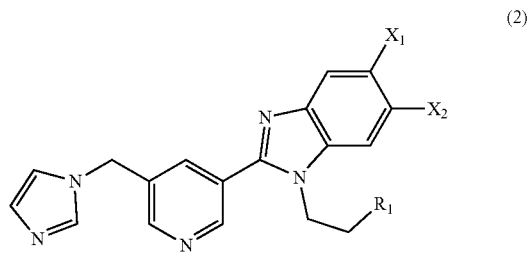

(2)

In the above formula (2), $X_1$ represents a hydrogen atom or a halogen atom, $X_2$ represents a fluorine atom or a nitrile group, and $R_1$ represents a halogen atom, a substituted or unsubstituted alkylsulfonyloxy group, or a substituted or unsubstituted arylsulfonyloxy group.

In another aspect of the present invention, a method for producing a radioactive compound represented by the above formula (1) or a salt thereof, by a radiohalogenation reaction, from the compound represented by the above formula (2) or a salt thereof can be provided.

According to the present invention, a compound having a specific and high binding ability to a human aldosterone-producing tumor, and a medicament including the same is provided.

BRIEF DESCRIPTION OF DRAWINGS

In FIG. 2C, the symbol "*" indicates that the number of experiment is one.

DESCRIPTION OF EMBODIMENTS

Figure 1:
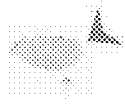
FIG. 1 is a set of autoradiograms obtained in Evaluation 1 of Examples by using Compounds [$^{18}$F]100 (control), [$^{18}$F]101, [$^{18}$F]102, and [$^{18}$F]103, respectively, in which Samples 1 to 6 each show a region of interest in a different lesion region, and the column on the left side of the column of Compound [$^{18}$F]100 (control) shows the results by immunohistochemical staining of the same samples. The autoradiograms in FIG. 1 are each an autoradiogram showing the accumulation of radioactivity in each region (lesion region, or normal region), which is shown on the same scale on the basis of a standard radiation source. Further, in FIG. 1, each arrow in the "immunohistochemical staining" column indicates a lesion region of a human aldosterone-producing tumor.
Figure 1:
Figure 1:
Figure 1:
Figure 1:
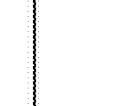
Figure 1:
Figure 1:
Figure 1:
Figure 1:
Figure 1:
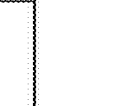
Figure 1:
Figure 1:
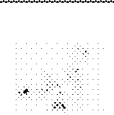
Figure 1:
Figure 1:
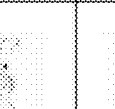
Figure 1:
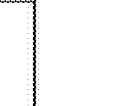
Figure 1:
Figure 1:
Figure 1:
Figure 1:
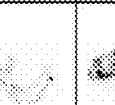
Figure 1:
Figure 1:
Figure 1:
Figure 1:
Figure 1:
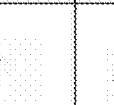
Figure 1:
Figure 1:
Figure 1:
Figure 1:
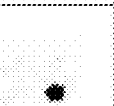
Figure 1:
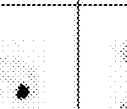
Figure 1:

In the present invention, the term "halogen atom" means at least one kind selected from a fluorine atom, a chlorine atom, a bromine atom, an iodine atom, and an astatine atom.

Further, in the present invention, the term "salt" may be any salt as long as the salt is acceptable as a medicament. As the salt, a salt derived from, for example, an inorganic acid such as hydrochloric acid, hydrobromic acid, sulfuric acid, nitric acid, or phosphoric acid, or an organic acid such as acetic acid, trifluoroacetic acid, maleic acid, succinic acid, mandelic acid, fumaric acid, malonic acid, pyruvic acid, oxalic acid, glycolic acid, salicylic acid, pyranosidyl acid (glucuronic acid, galacturonic acid, or the like), α-hydroxy acid (citric acid, tartaric acid, or the like), amino acid (aspartic acid, glutamic acid, or the like), aromatic acid (benzoic acid, cinnamic acid, or the like), or sulfonic acid (p-toluenesulfonic acid, ethanesulfonic acid, or the like), can be used.

In the present invention, the term "radioactive halogen atom" means at least one kind selected from radioactive isotopes of fluorine, chlorine, bromine, and iodine, and as the radioactive halogen atom, preferably, $^{18}$F, $^{34m}$Cl, $^{76}$Br, $^{123}$I, $^{124}$I, or $^{125}$I can be used. In this regard, in the present invention, the term "radioactive iodine atom" means any one of $^{123}$I, $^{124}$I, or $^{125}$I.

From the viewpoint of increasing the binding ability to an aldosterone-producing tumor, in the above formula (1) wherein $X_1$ is a hydrogen atom, $X_2$ is preferably a fluorine atom. Further, from the similar point of view, in the above formula (1) wherein $X_1$ is a halogen atom, $X_2$ is preferably a fluorine atom or a nitrile group. Furthermore, from the similar point of view, in the above formula (1) where $X_1$ is a fluorine atom, $X_2$ is preferably to a fluorine atom or a nitrile group.

In the above formula (1), by using a radioactive halogen atom as the halogen atom of $X_3$, the compound can be applied to the use as a diagnostic imaging agent for nuclear medicine examination.

As a preferred aspect of the compound according to the present invention, three compounds represented by the following chemical formulas can be mentioned.

(Compound 101)

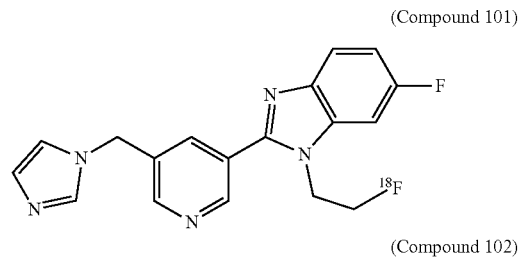

(Compound 102)

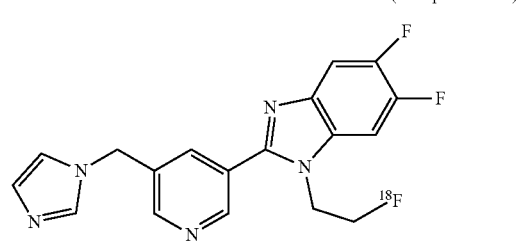

(Compound 103)

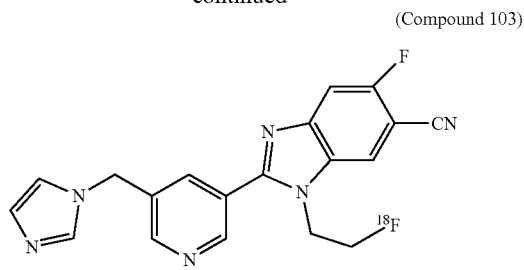

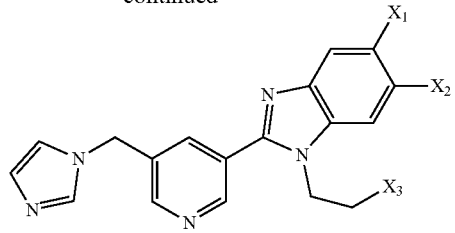

In the present invention, as the substituted or unsubstituted alkylsulfonyloxy group, an alkylsulfonyloxy group having 1 to 12 carbon atoms is preferred. In the substituted alkylsulfonyloxy group, a hydrogen atom in the alkyl chain may be replaced with a halogen atom. Further, in the present invention, as the substituted or unsubstituted arylsulfonyloxy group, a substituted or unsubstituted benzenesulfonyloxy group is preferred, and a substituted benzenesulfonyloxy group is more preferred. In the substituted arylsulfonyloxy group, a hydrogen atom in the aryl ring is preferably replaced with an alkyl group having 1 to 12 carbon atoms, or a nitro group. Preferred specific examples of the substituted or unsubstituted alkylsulfonyloxy group and substituted or unsubstituted arylsulfonyloxy group include methanesulfonyloxy group, benzenesulfonyloxy group, p-toluenesulfonyloxy group, p-nitrobenzenesulfonyloxy group, and trifluoromethanesulfonyloxy group.

Hereafter, an example of the method for producing the radioactive compound represented by the above formula (1) will be described with reference to the following Scheme 1. A compound represented by the above formula (1) in which $X_3$ is a hydroxy group is used as a starting material, and into the hydroxy group, a group represented by $R_1$ of the above formula (2) (a halogen atom, a substituted or unsubstituted alkylsulfonyloxy group, or a substituted or unsubstituted arylsulfonyloxy group) is introduced to obtain a compound represented by the above formula (2) as a labeling precursor (Step a in Scheme 1). Next, a nucleophilic substitution reaction is conducted on the group represented by $R_1$ using a radioactive halide ion to obtain a radioactive compound represented by the above formula (1) (Step b in Scheme 1).

Scheme 1

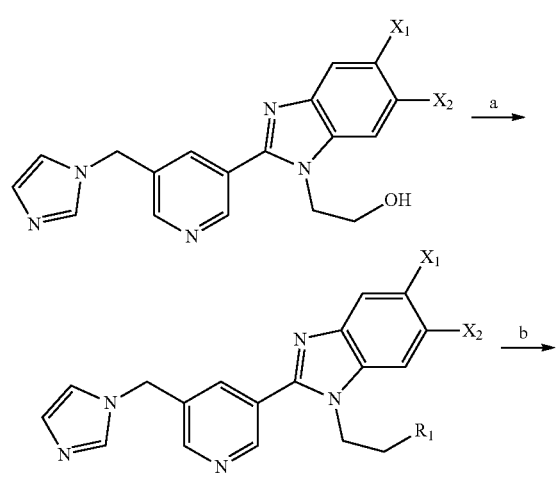

In this regard, examples of the "radioactive halide ion" include a radioactive fluoride ion (for example, $[^{18}F]$ fluoride ion), a radioactive chloride ion (for example, $[^{34m}Cl]$ chloride ion), a radioactive bromide ion (for example, $[^{76}Br]$ bromide ion), and a radioactive iodide ion (for example, $[^{123}I]$ iodide ion, $[^{124}I]$ iodide ion, or $[^{125}I]$ iodide ion). In a case where a radioactive fluoride ion is used, the labeling precursor is preferably a compound represented by the above formula (2) in which $R_1$ represents a chlorine atom, a bromine atom, an iodine atom, a substituted or unsubstituted alkylsulfonyloxy group, or a substituted or unsubstituted arylsulfonyloxy group. Further, in a case where a radioactive chloride ion is used, the labeling precursor is preferably a compound represented by the above formula (2) in which $R_1$ represents a bromine atom, an iodine atom, a substituted or unsubstituted alkylsulfonyloxy group, or a substituted or unsubstituted arylsulfonyloxy group. Furthermore, in a case where a radioactive bromide ion is used, the labeling precursor is preferably a compound represented by the above formula (2) in which $R_1$ represents an iodine atom, a substituted or unsubstituted alkylsulfonyloxy group, or a substituted or unsubstituted arylsulfonyloxy group. Moreover, in a case where a radioactive iodide ion is used, the labeling precursor is preferably a compound represented by the above formula (2) in which $R_1$ represents a substituted or unsubstituted alkylsulfonyloxy group, or a substituted or unsubstituted arylsulfonyloxy group is preferred. The nucleophilic substitution reaction using such a radioactive halide ion is preferably conducted in the presence of a base such as an alkali metal carbonate (for example, sodium carbonate, or potassium carbonate).

For example, by conducting a radioactive fluorination reaction using a radioactive fluoride ion, a radioactive compound represented by the above formula (1) in which $X_3$ is a radioactive fluorine atom can be obtained. The radioactive fluorination reaction is preferably conducted in the presence of a base, and may also be conducted in a presence of various kinds of phase transfer catalysts, for example, 4,7,13,16,21,24-hexaoxa-1,10-diazabicyclo[8.8.8]-hexacosane (trade name: Kryptofix 222).

In a case where a radioactive compound represented by the above formula (1) or a salt thereof is used as a medicament, it is desired to purify unreacted radioactive halogen and insoluble impurities after radiohalogenation reaction, using by a membrane filter, a column filled with various fillers, HPLC, or the like.

In the present invention, a medicament can also be prepared from the compound thus produced or a salt thereof.

In the present specification, the term "medicament" can be defined as a preparation containing a compound represented by the above formula (1) or a salt thereof in a form suitable for administration into a living body. This medicament can be administered orally or parenterally (for example, intravenously, subcutaneously, intramuscularly, intrathecally, topically, transrectally, transdermally, transnasally, or transpulmonarily). Examples of the dosageform for oral administration include dosage forms such as a tablet, a capsule, a pill, granules, fine granules, a powder, a liquid, a syrup, and a suspension. Further, examples of the dosage form for parenteral administration include forms such as an aqueous preparation for injection, an oily preparation for injection, a suppository, a transnasal preparation, and a transdermal absorption preparation (lotion, emulsion, ointment, cream, jelly, gel, a patch preparation such as tape, a transdermal patch, or a poultice, a powder for external use, or the like).

The medicament according to the present invention is prepared by using a conventionally-known technique, and can contain a nontoxic and inert carrier that is usually used in the field of pharmaceuticals. The carrier that can be contained in the medicament according to the present invention is not limited as long as it is a substance commonly used in the field of pharmaceuticals and does not react with a compound represented by the above formula (1) or a salt thereof, and examples of the carrier include an excipient, a binding agent, a lubricating agent, a stabilizer, a disintegrant, a buffer agent, a solubilizer, an isotonizing agent, a solubilizer, a pH regulator, a surfactant, an emulsifier, a suspending agent, a dispersant, a precipitation-preventing agent, a thickener, a viscosity modifier, a gelling agent, an analgesic, a preservative, a plasticizer, a transdermal absorption promoting agent, an antioxidant, a moisturizer, an antiseptic, and a flavor. These carriers may be used in appropriate combination of two or more kinds thereof.

In addition, if the medicament according to the present invention is administered into a living body, the medicament can specifically highly accumulate in an aldosterone-producing tumor. For this reason, with the use of a radioactive halogen atom as the halogen atom of $X_3$ in the above formula (1), an aldosterone-producing tumor or adrenal gland disease can be imaged by noninvasively detecting radiation from the outside of the living body by using a radiation detector, a single-photon emission computed tomography scanner, a positron emission tomography scanner, scintigraphy, or the like. Accordingly, the medicament according to the present invention can be used as a diagnostic imaging agent for nuclear medicine examination, and specifically can be used for the application of a diagnostic imaging agent for positron emission tomography (PET), or a diagnostic imaging agent for single-photon emission computed tomography (SPECT). For example, in a case where a positron-emitting nuclide such as $^{18}F$, $^{76}Br$, or $^{124}I$ is used as a radioactive halogen atom, the medicament according to the present invention can be used as a diagnostic imaging agent for positron emission tomography, and in a case where $^{123}I$ is used as a radioactive halogen atom, the medicament according to the present invention can be used as a diagnostic imaging agent for single-photon emission computed tomography. Further, by using an element suitable for the nuclear magnetic signal measurement, such as $^{19}F$ as a halogen atom of $X_3$ in the above formula (1), an aldosterone-producing tumor can also be imaged with the use of a nuclear magnetic resonance imaging (MRI) device.

EXAMPLES

Hereinafter, the present invention will be described in more detail by describing Examples, but the present invention is not limited to these contents.

In Examples, the molecular structure of each compound was identified by a $^1$H-NMR spectrum. AVANCE III (manufactured by Bruker Corporation) was used as an NMR device, the resonance frequency was set to 500 MHz, tetramethylsilane (TMS) was used as an internal standard, and the TMS resonance was set to 0.00 ppm. All chemical shifts were in ppm on the delta scale (δ), and the fine splitting of the signals is indicated by using abbreviations (s: singlet, d: doublet, t: triplet, dd: double doublet, dt: double triplet, m: multiplet, bs: broad singlet, and quin: quintet).

Hereinafter, the term "room temperature" indicates 25° C. in Examples.

In a synthesis example of each compound, each step in the compound synthesis was repeatedly conducted as needed to ensure the amount required for use as an intermediate or the like in other syntheses.

(Reference Example 1) Synthesis of Compound 100

Compound 100 was synthesized according to the scheme shown in FIG. 1 of International Publication No. WO 2015/199205 A.

(Reference Example 2) Synthesis of Compound [$^{18}$F]100

Figure 2A:
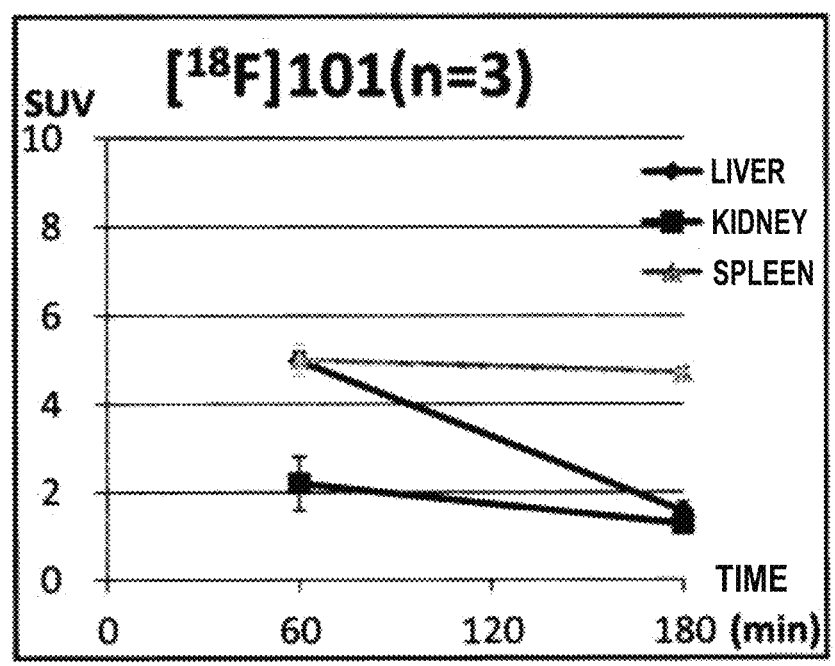
FIG. 2A is a graph showing the time course of biodistributions of Compound [$^{18}$F]101 obtained in Examples in the liver, kidney and spleen.
Figure 2B:
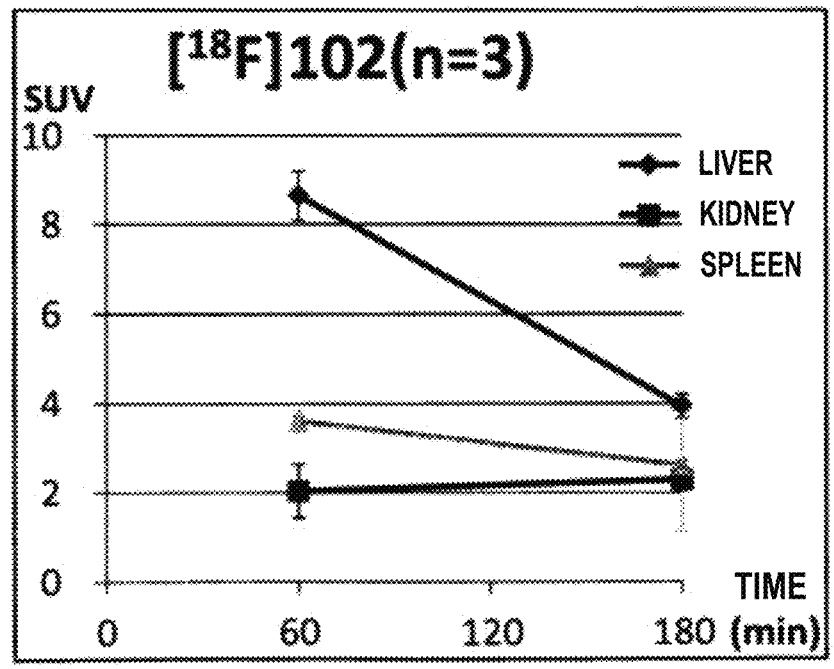
FIG. 2B is a graph showing the time course of biodistributions of Compound [$^{18}$F]102 obtained in Examples in the liver, kidney and spleen.
Figure 2C:
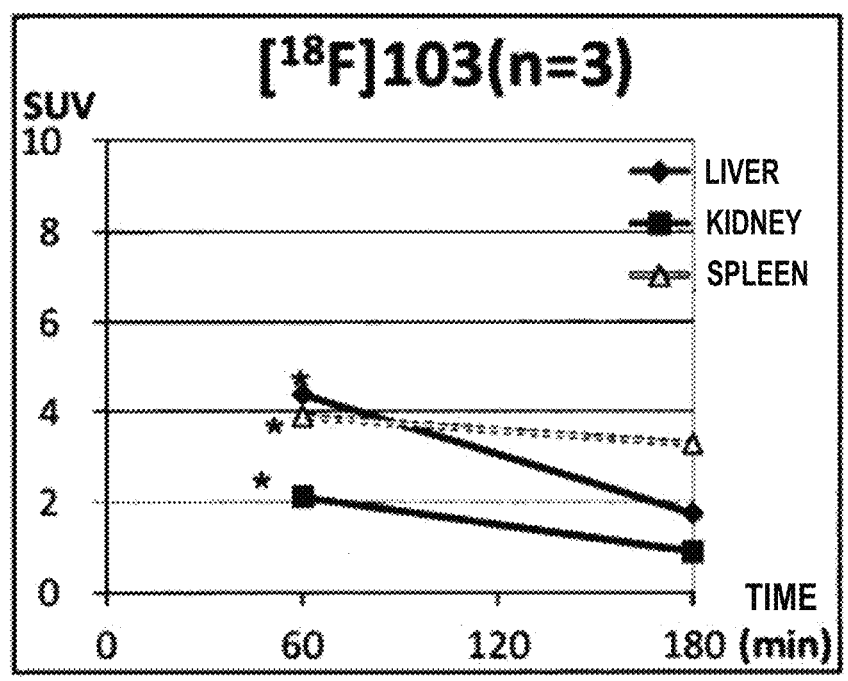
FIG. 2C is a graph showing the time course of biodistributions of Compound [$^{18}$F]103 obtained in Examples in the liver, kidney and spleen.

Compound [$^{18}$F]100 was synthesized according to the scheme shown in FIG. 2 of International Publication No. WO 2015/199205 A.

(Example 1) Synthesis of Compound 1

Compound 101 was synthesized according to the following Scheme 2.

Synthesis of N-(5-fluoro-2-nitrophenyl)-2-fluoroethylamine (Compound 2)

2,4-Difluoronitrobenzene (Compound 1) (109.7 μL, 1.0 mmol) was dissolved in dichloromethane (3.0 mL), and then into the obtained mixture, potassium carbonate (691.0 mg, 5.0 mmol) and 2-fluoroethylamine (298.6 mg, 3.0 mmmol) were added under an argon gas atmosphere and ice cooling, and the resultant mixture was stirred at room temperature for 2 days. After completion of the reaction, water was added at room temperature, and then extracted three times with dichloromethane. The combined dichloromethane layer was dried over anhydrous sodium sulfate and then concentrated under reduced pressure, the obtained crude product was purified by silica gel chromatography (eluent: n-hexane/ethyl acetate=20/1→10/1) to obtain N-(5-fluoro-2-nitrophenyl)-2-fluoroethylamine (Compound 2) (231.2 mg, 1.14 mmol).

$^1$H-NMR of Compound 2 (solvent: deuterated chloroform): δ 8.36 (bs, 1H), 8.25 (dd, J=9.5, 6.1 Hz, 1H), 6.52 (dd, J=11.3, 2.6 Hz, 1H), 6.44-6.41 (m, 1H), 4.70 (dt, J=47, 5.0 Hz, 2H), 3.62 (dq, J=25, 4.1 Hz, 2H).

Synthesis of 3-fluoro-N-[2-fluoroethyl]-1,6-phenylenediamine (Compound 3)

N-(5-Fluoro-2-nitrophenyl)-2-fluoroethylamine (Compound 2) (231.2 mg, 1.14 mmol) was dissolved in ethyl acetate (4.0 mL), and then, tin(II) chloride (867.4 mg, 4.57 mmol) and water (82.3 μL, 4.57 mmol) were added, and heated under reflux for 8 hours under an argon gas atmosphere. After completion of the reaction, a 4 M aqueous sodium hydroxide solution was added, and the deposited precipitate was filtered, and the obtained filtrate was extracted three times with ethyl acetate. The combined ethyl acetate layer was dried over anhydrous sodium sulfate and then concentrated under reduced pressure, the obtained crude product was purified by silica gel chromatography (eluent: n-hexane/ethyl acetate=5/1→2/1) to obtain 3-fluoro-N-[2-fluoroethyl]-1,6-phenylenediamine (Compound 3) (137.9 mg, 0.801 mmol).

$^1$H-NMR of Compound 3 (solvent: deuterated chloroform): δ 6.66-6.63 (m, 1H), 6.39-6.35 (m, 2H), 4.67 (dt, J=47, 4.9 Hz, 2H), 3.41 (dt, J=27, 4.8 Hz, 1H), 3.18 (bs, 2H).

Synthesis of 5-{6-fluoro-1-[2-fluoroethyl]benzimidazol-2-yl}pyridine-3-methanol (Compound 4)

5-Hydroxymethyl-3-pyridinecarboxaldehyde (109.9 mg, 0.801 mmmol) was dissolved in N,N'-dimethylformamide (1 mL), and then a N,N'-dimethylformamide solution (2 mL), in which 3-fluoro-N-[2-fluoroethyl]-1,6-phenylenediamine (Compound 3) (137.9 mg, 0.801 mmol) had been dissolved, and Oxone (registered trademark) monopersulfate compound (590.8 mg, 0.961 mmol) were added under ice cooling, and the resultant mixture was stirred at room temperature for 2 hours and 30 minutes under an argon gas atmosphere. After completion of the reaction, a saturated aqueous solution of sodium thiosulfate and a saturated aqueous solution of sodium hydrogen carbonate were added under ice cooling, and extracted three timeds with ethyl acetate. The combined ethyl acetate layer was dried over anhydrous sodium sulfate and then concentrated under reduced pressure, the obtained crude product was purified by silica gel chromatography (eluent: ethyl acetate/n-hexane/methanol=10/5/1) to obtain 5-{6-fluoro-1-[2-fluoroethyl]benzimidazol-2-yl}pyridine-3-methanol (Compound 4) (148.7 mg, 0.514 mmol).

$^1$H-NMR of Compound 4 (solvent: deuterated chloroform): δ 8.87 (d, J=2.1 Hz, 1H), 8.76 (d, J=2.1 Hz, 1H), 8.13 (t, J=2.1 Hz, 1H), 7.78 (dd, J=8.9, 4.9 Hz, 1H), 7.15-7.09 (m, 2H), 4.86 (d, J=5.6 Hz, 2H), 4.80 (dt, J=47, 4.8 Hz, 2H), 4.50 (dt, J=25, 4.8 Hz, 2H).

Synthesis of 6-fluoro-1-(2-fluoroethyl)-2-[5-(imidazol-1-ylmethyl)pyridin-3-yl]benzimidazole (Compound 101)

5-{6-Fluoro-1-[2-fluoroethyl]benzimidazol-2-yl}pyridine-3-methanol (Compound 4) (148.7 mg, 0.514 mmol) was dissolved in tetrahydrofuran (5 mL), and then into the obtained mixture, triethylamine (214.3 μL, 1.54 mmol) was added. Further, p-toluenesulfonic acid anhydride (335.5 mg, 1.03 mmol) was added at −20° C., and the resultant mixture was stirred at −20° C. for 4 hours under an argon gas atmosphere. Furthermore, triethylamine (214.3 μL, 1.54 mmol) and p-toluenesulfonic acid anhydride (335.5 mg, 1.03 mmol) were added, and the resultant mixture was stirred at −20° C. for 3 hours under an argon gas atmosphere. After completion of the reaction, triethylamine (1.1 mL, 7.71 mmol) and imidazole (349.9 mg, 5.14 mmol) were added, and the resultant mixture was stirred at room temperature overnight under an argon gas atmosphere. After completion of the reaction, the mixture was purified by silica gel chromatography (eluent: chloroform/methanol=20/1), the obtained fraction was concentrated under reduced pressure, and the concentrated fraction was dissolved in ethyl acetate, and the resultant mixture was washed with a saturated aqueous solution of sodium hydrogen carbonate. Subsequently, the washed ethyl acetate layer was dried over anhydrous sodium sulfate and then concentrated to obtain 6-fluoro-1-(2-fluoroethyl)-2-[5-(imidazol-1-yl-methyl)pyridin-3-yl]benzimidazole (Compound 101) (31.5 mg, 0.0931 mmol).

$^1$H-NMR of Compound 101 (solvent: deuterated chloroform): δ 8.94 (d, J=2.0 Hz, 1H), 8.64 (d, J=2.2 Hz, 1H), 7.87 (t, J=1.9 Hz, 1H), 7.77 (dd, J=9.5, 4.9 Hz, 1H), 7.62 (s, 1H), 7.14 (s, 1H), 7.13-7.09 (m, 2H), 6.96 (t, J=1.3 Hz, 1H), 5.26 (s, 2H), 4.77 (dt, J=47, 4.7 Hz, 2H), 4.42 (dt, J=25, 4.8 Hz, 2H).

(Example 2) Synthesis of Compound [$^{18}$F]101

Compound [$^{18}$F]101 was synthesized according to the following Scheme 2.

Synthesis of 2-(tert-butyldiphenylsilyloxy)ethylamine (Compound 6)

2-Amino ethanol (Compound 5) (2.2 mL, 40.0 mmol) was dissolved in dichloromethane (100 mL), and then tert-butyldiphenylsilyl chloride (15.6 mL, 60.0 mmol) and imidazole (5.44 g, 80.0 mmol) were added under room temperature, and the resultant mixture was stirred at room temperature overnight under an argon gas atmosphere. After completion of the reaction, water was added under ice cooling, and then extracted three times with dichloromethane. The combined dichloromethane layer was dried over anhydrous sodium sulfate, and then concentrated under reduced pressure to obtain a crude product, and the crude product was purified by silica gel chromatography (eluent: ethyl acetate→ethyl acetate/methanol=10/1→5/1) to obtain 2-(tert-butyldiphenylsilyloxy)ethylamine (Compound 6) (12.2 g, 40.7 mmol).

$^1$H-NMR of Compound 6 (solvent: deuterated chloroform): δ 7.67-7.65 (m, 4H), 7.44-7.36 (m, 6H), 3.70 (t, J=5.3 Hz, 2H), 2.84 (t, J=5.3 Hz, 2H), 2.79 (bs, 2H), 3.08 (bs, 2H), 1.07 (s, 9H).

Synthesis of N-(5-fluoro-2-nitrophenyl)-2-(tert-butyldiphenylsilyloxy)ethylamine (Compound 7)

2,4-Difluoronitrobenzene (Compound 1) (66.9 μL, 0.606 mmol) was dissolved in dichloromethane (2.0 mL), and then, potassium carbonate (420.5 mg, 3.04 mmol) and 2-(tert-butyldiphenylsilyloxy)ethylamine (Compound 6) (546.7 mg, 1.83 mmol) were added under an argon gas atmosphere and ice cooling, and the resultant mixture was stirred at room temperature overnight. After completion of the reaction, into the mixture, water was added at room temperature, and then extracted three times with dichloromethane. The combined dichloromethane layer was dried over anhydrous sodium sulfate and then concentrated under reduced pressure, the obtained crude product was purified by silica gel chromatography (eluent: n-hexane/ethyl acetate=20/1→10/1) to obtain N-(5-fluoro-2-nitrophenyl)-2-(tert-butyldiphenyl-silyloxy)ethylamine (Compound 7) (286.9 mg, 0.654 mmol).

$^1$H-NMR of Compound 7 (solvent: deuterated chloroform): δ 8.51 (bs, 1H), 8.22 (dd, J=9.5, 6.2 Hz, 1H), 7.67-7.65 (m, 4H), 7.43-7.36 (m, 6H), 6.43 (dd, J=11.5, 2.6 Hz, 1H), 6.37-6.33 (m, 1H), 3.90 (t, J=5.4 Hz, 2H) , 3.47 (q, J=5.4 Hz, 2H) , 1.07 (s, 9H).

Synthesis of 3-fluoro-N-[2-(tert-butyldiphenyl-silyloxy)ethyl]-1,6-phenylenediamine (Compound 8)

N-(5-Fluoro-2-nitrophenyl)-2-(tert-butyldiphenyl-silyloxy)ethylamine (Compound 7) (286.9 mg, 0.654 mmol)

was dissolved in methanol (3.0 mL), and then, 10% palladium carbon (11.2 mg) was added under an argon gas atmosphere. Subsequently, the resultant mixture was stirred at room temperature overnight under a hydrogen gas atmosphere. After completion of the reaction, the mixture was filtered through Celite, the filtrate was concentrated under reduced pressure, and the obtained crude product was purified by silica gel chromatography (eluent: n-hexane/ethyl acetate=20/1→5/1) to obtain 3-fluoro-N-[2-(tert-butyldiphenylsilyloxy)ethyl]-1,6-phenylenediamine (Compound 8) (122.4 mg, 0.300 mmol).

$^1$H-NMR of Compound 8 (solvent: deuterated chloroform): δ 7.67 (dd, J=6.0, 1.3 Hz, 4H), 7.43-7.41 (m, 2H), 7.39-7.36 (m, 4H), 6.62 (dd, J=8.3, 5.7 Hz, 1H), 6.34-6.28 (m, 2H), 4.16 (bs, 1H), 3.91 (t, J=5.4 Hz, 2H), 3.21 (q, J=5.2 Hz, 2H), 3.08 (bs, 2H), 1.07 (s, 9H).

Synthesis of 5-{6-fluoro-1-[2-(tert-butyldiphenylsilyloxy)ethyl]benzimidazol-2-yl}pyridine-3-methanol (Compound 9)

5-Hydroxymethyl-3-pyridinecarboxaldehyde (40.8 mg, 0.298 mol) was dissolved in N,N'-dimethylformamide (0.5 mL), and then, under ice cooling, 3-fluoro-N-[2-(tert-butyldiphenylsilyloxy)ethyl]-1,6-phenylenediamine (Compound 8) (122.4 mg, 0.300 mol) and Oxone (registered trademark) monopersulfate compound (221.3 mg, 0.360 mmol) were added, and the resultant mixture was stirred at room temperature for 30 minutes under an argon gas atmosphere. After completion of the reaction, into the mixture, a saturated aqueous solution of sodium thiosulfate and a saturated aqueous solution of sodium hydrogen carbonate were added under ice cooling, and then extracted three times with ethyl acetate. The combined ethyl acetate layer was dried over anhydrous sodium sulfate and then concentrated under reduced pressure, the obtained crude product was purified by silica gel chromatography (eluent: ethyl acetate/n-hexane/methanol=10/5/1) to obtain 5-{6-fluoro-1-[2-(tert-butyldiphenylsilyloxy)ethyl]benzimidazol-2-yl}pyridine-3-methanol (Compound 9) (131.3 mg, 0.250 mmol).

$^1$H-NMR of Compound 9 (solvent: deuterated chloroform): δ 8.96 (d, J=2.1 Hz, 1H), 8.73 (d, J=2.1 Hz, 1H), 8.12 (t, J=2.1 Hz, 1H), 7.77 (dd, J=8.8, 4.8 Hz, 1H), 7.38-7.36 (m, 6H), 7.29-7.28 (m, 4H), 7.09-7.05 (m, 1H), 6.91 (dd, J=8.7, 2.4 Hz, 1H), 4.76 (d, J=5.8 Hz, 2H), 4.40 (t, J=5.7 Hz, 2H), 3.94 (t, J=5.7 Hz, 2H), 0.89 (s, 9H).

Synthesis of 6-fluoro-2-[5-(imidazol-1-ylmethyl) pyridin-3-yl]-1-[2-(tert-butyldiphenylsilyloxy)ethyl] benzimidazole (Compound 10)

5-{6-Fluoro-1-[2-(tert-butyldiphenyl-silyloxy)ethyl]benzimidazol-2-yl}pyridine-3-methanol (Compound 9) (131.3 mg, 0.250 mmol) was dissolved in dichloromethane (2.5 mL), and then under ice cooling, triethylamine (104.4 µL, 0.750 mmol) and p-toluenesulfonic acid anhydride (163.0 mg, 0.500 mmol) were added, the resultant mixture was stirred at room temperature for one hour and 30 minutes under an argon gas atmosphere. After completion of the reaction, water was added, and extracted three times with dichloromethane. The combined dichloromethane layer was dried over anhydrous sodium sulfate and then concentrated under reduced pressure to obtain a crude product. Imidazole (85.0 mg, 1.25 mmol) was dissolved in N,N'-dimethylformamide (0.2 mL), and then the obtained mixture was ice-cooled. Into the resultant mixture, triethylamine (174.1 µL, 1.25 mmol) was added, and then the previously obtained crude product that had been dissolved in N,N'-dimethylformamide (0.8 mL) was added, and the resultant mixture was stirred at room temperature for 4 hours under an argon gas atmosphere. After completion of the reaction, into the mixture, water was added, and extracted three times with ethyl acetate. The combined ethyl acetate layer was dried over anhydrous sodium sulfate and then concentrated under reduced pressure, the obtained crude product was purified by silica gel chromatography (eluent: dichloromethane/methanol=30/1→20/1→10/1) to obtain 6-fluoro-2-[5-(imidazol-1-ylmethyl)pyridin-3-yl]-1-[2-(tert-butyldiphenylsilyloxy) ethyl]benzimidazole (Compound 10) (128.1 mg, 0.222 mmol).

$^1$H-NMR of Compound 10 (solvent: deuterated chloroform): δ 9.06 (d, J=2.2 z, 1H), 8.55 (d, J=2.2 Hz, 1H), 7.92 (t, J=2.2 Hz, 1H), 7.76 (dd, J=8.8, 4.8 Hz, 1H), 7.55 (s, 1H), 7.40-7.35 (m, 6H), 7.29-7.27 (m, 4H), 7.09-7.05 (m, 2H), 6.90-6.86 (m, 2H), 5.13 (s, 2H), 4.34 (t, J=5.5 Hz, 2H) , 3.94 (t, J=5.5 Hz, 2H) , 0.89 (s, 9H).

Synthesis of 2-{6-fluoro-2-[5-(imidazol-1-ylmethyl) pyridin-3-yl]benzimidazol-1-yl}ethanol (Compound 11)

6-Fluoro-2-[5-(imidazol-1-ylmethyl)pyridin-3-yl]-1-[2-(tert-butyldiphenylsilyloxy)ethyl]benzimidazole (Compound 10) (128.1 mg, 0.222 mmol) was dissolved in tetrahydrofuran (2.0 mL), and thentetrabutylammonium fluoride (0.33 mL, tetrahydrofuran solution, around 1 M, 0.33 mmol) was added at room temperature, and the resultant mixture was stirred at room temperature for one hour and 30 minutes under an argon gas atmosphere. After completion of the reaction, the reaction solution was concentrated under reduced pressure, and the obtained crude product was purified by silica gel chromatography (eluent: dichloromethane/methanol=20/1→10/1→5/1) to obtain 2-{6-fluoro-2-[5-(imidazol-1-ylmethyl)pyridin-3-yl]benzimidazol-1-yl}ethanol (Compound 11) (25.8 mg, 0.0765 mmol).

$^1$H-NMR of Compound 11 (solvent: deuterated chloroform): δ 9.07 (d, J=2.2 Hz, 1H), 8.64 (d, J=2.2 Hz, 1H), 7.87 (t, J=2.2 Hz, 1H), 7.73 (dd, J=8.9, 4.8 Hz, 1H), 7.62 (s, 1H), 7.15 (d, J=2.4 Hz, 1H), 7.13 (s, 1H), 7.12 (dt, J=10.3, 2.4 Hz, 1H), 6.98 (t, J=1.3 Hz, 1H), 5.27 (s, 2H), 4.21 (t, J=5.7 Hz, 2H), 3.99 (t, J=5.7 Hz, 2H), 2.44 (bs, 1H).

Synthesis of 6-chloro-5-fluoro-2-[5-(imidazol-1-ylmethyl)pyridin-3-yl]-1-[2-(p-toluenesulfonyloxy) ethyl]benzimidazole (Compound 12)

2-{6-Fluoro-2-[5-(imidazol-1-ylmethyl)pyridin-3-yl]benzimidazol-1-yl}ethanol (Compound 11) (20.0 mg, 0.0593 mmol) was dissolved in dichloromethane (1.0 mL), and then p-toluenesulfonyl chloride (22.6 mg, 0.119 mol) and triethylamine (24.8 µL, 0.176 mmol) were added, and the resultant mixture was stirred at room temperature for 3 hours under an argon gas atmosphere. After completion of the reaction, the mixture was purified by silica gel chromatography (eluent: chloroform/methanol=20/1→10/1), the obtained fraction was concentrated under reduced pressure, and the concentrated fraction was dissolved in ethyl acetate, and the resultant mixture was washed with water. Subsequently, the washed ethyl acetate layer was dried over anhydrous sodium sulfate and then concentrated to obtain 6-fluoro-2-[5-(imidazol-1-ylmethyl)pyridin-3-yl]-1-[2-(p-toluenesulfonyloxy)ethyl]benzimidazole (Compound 12) (10.9 mg, 0.0229 mmol).

¹H-NMR of Compound 12 (solvent: deuterated methanol): δ 8.82 (d, J=2.1 Hz, 1H), 8.70 (d, J=2.1 Hz, 1H), 8.02 (t, J=2.1 Hz, 1H), 7.90 (s, 1H), 7.62 (dd, J=8.8, 4.7 Hz, 1H), 7.28 (dd, J=6.4, 1.8 Hz, 3H), 7.21 (dd, J=8.9, 2.4 Hz, 1H), 7.13-7.10 (m, 1H), 7.06 (t, J=2.3 Hz, 3H), 5.46 (s, 2H), 4.49 (t, J=5.9 Hz, 2H), 4.25 (t, J=5.9 Hz, 2H), 2.32 (s, 3H).

Synthesis of Compound [¹⁸F]101

[¹⁸F] Fluoride ion-containing $H_2{}^{18}O$ (the amount of radioactivity: 2330 MBq, correction value at the start of synthesis) was allowed to pass through a Sep-Pak column (trade name: Sep-Pak (registered trademark) Light Cartridge Accell (registered trademark) Plus QMA Carbonate, manufactured by Waters Corporation, the amount of filler: 130 mg), and [¹⁸F] fluoride ions were adsorbed and collected on the column. A potassium carbonate aqueous solution (42.4 μmol/L, 0.3 mL) and a solution (0.7 mL) of Kryptofix 222 (trade name, manufactured by MerckKGaA) (14 mg, 37.2 μmol) in acetonitrile were allowed to pass through the column to elute the [¹⁸F] fluoride ions. The obtained eluate was heated to 110° C. under an argon gas flow to evaporate water, and then acetonitrile (0.5 mL×2) was added thereto, and the resultant mixture was azeotropically evaporated to dryness. To the obtained product, a dimethyl sulfoxide solution (0.6 mL) in which 6-chloro-5-fluoro-2-[5-(imidazol-1-ylmethyl)pyridin-3-yl]-1-[2-(p-toluenesulfonyloxy) ethyl]benzimidazole (Compound 12) (3 mg, 0.0102 mmol) had been dissolved was added, and heated at 100° C. for 6 minutes. After completion of the reaction, into the mixture, water for injection (2.0 mL) was added, and the fraction of 6-fluoro-1-(2-[¹⁸F]fluoroethyl)-2-[5-(imidazol-1-ylmethyl) pyridin-3-yl]benzimidazole (Compound [¹⁸F]101) was separated by HPLC under the following conditions.

HPLC Conditions

Column: Develosil RPAQUEOUS (trade name, manufactured by Nomura Chemical Co., Ltd., size: 10×250 mm)

Mobile phase: 10 mM ammonium bicarbonate solution/acetonitrile=70/30

Flow rate: 4.0 mL/min

Detector: ultraviolet-visible absorption photometer (detection wavelength: 254 nm)

A liquid obtained by adding 10 mL of water to the fraction was allowed to pass through a Sep-Pak C18 column (trade name: Sep-Pak (registered trademark) Light C18 Cartridges, manufactured by Waters Corporation, the amount of filler: 130 mg), and 6-fluoro-1-(2-[¹⁸F]fluoroethyl)-2-[5-(imidazol-1-ylmethyl)pyridin-3-yl]benzimidazole (Compound [¹⁸F]101) was adsorbed and collected on the column. The column was washed with 5 mL of water, and then 1 mL of ethanol was allowed to pass through the column to elute 6-fluoro-1-(2-[¹⁸F]fluoroethyl)-2-[5-(imidazol-1-ylmethyl) pyridin-3-yl]benzimidazole (Compound [¹⁸F]101), and an ethanol solution of 6-fluoro-1-(2-[¹⁸F]fluoroethyl)-2-[5-(imidazol-1-ylmethyl)pyridin-3-yl]benzimidazole (Compound [¹⁸F]101) was obtained. The amount of the obtained radioactivity was 707 MBq immediately after the synthesis (49 minutes after the start of the synthesis). Further, when the TLC analysis was conducted under the following conditions, the radiochemical purity was 98.3%.

TLC Analysis Conditions

TLC plate: Silica Gel 60 $F_{254}$ (product name, manufactured by Merck KGaA)

Development phase: acetonitrile/water/diethylamine=10/1/1

RI detector: Rita Star, manufactured by Raytest GmbH

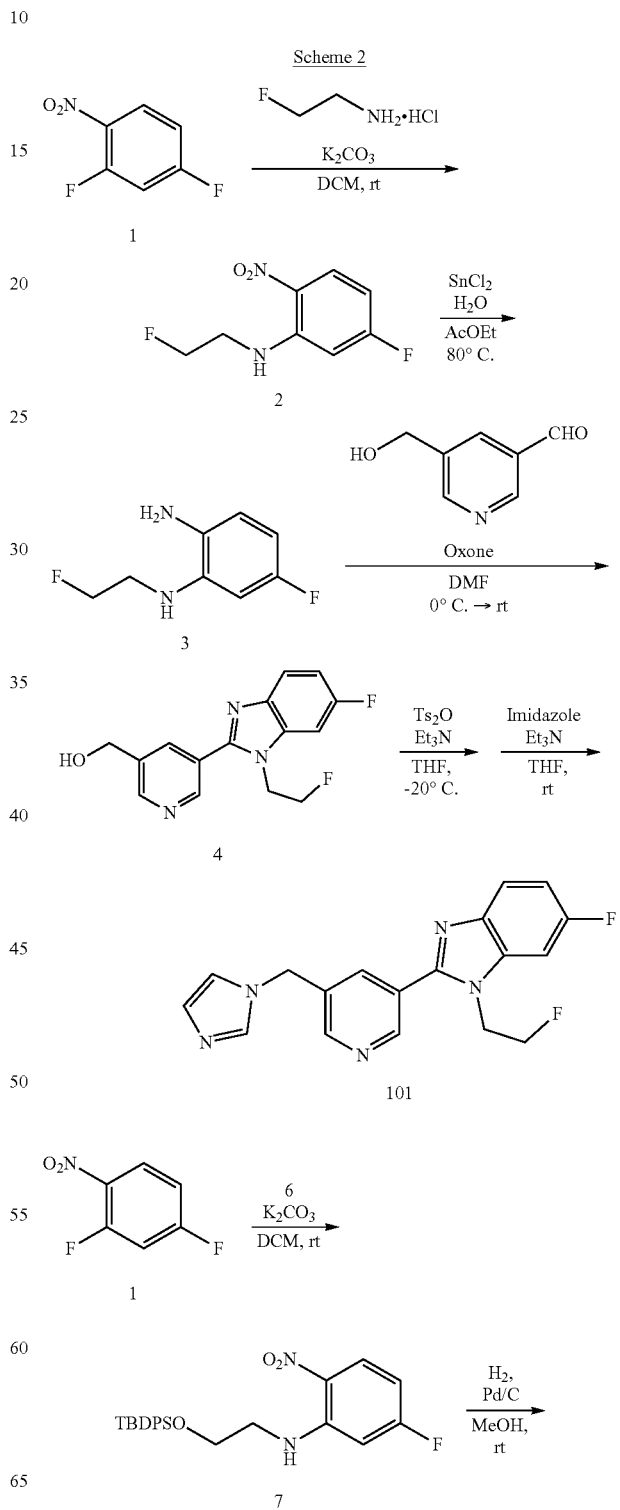

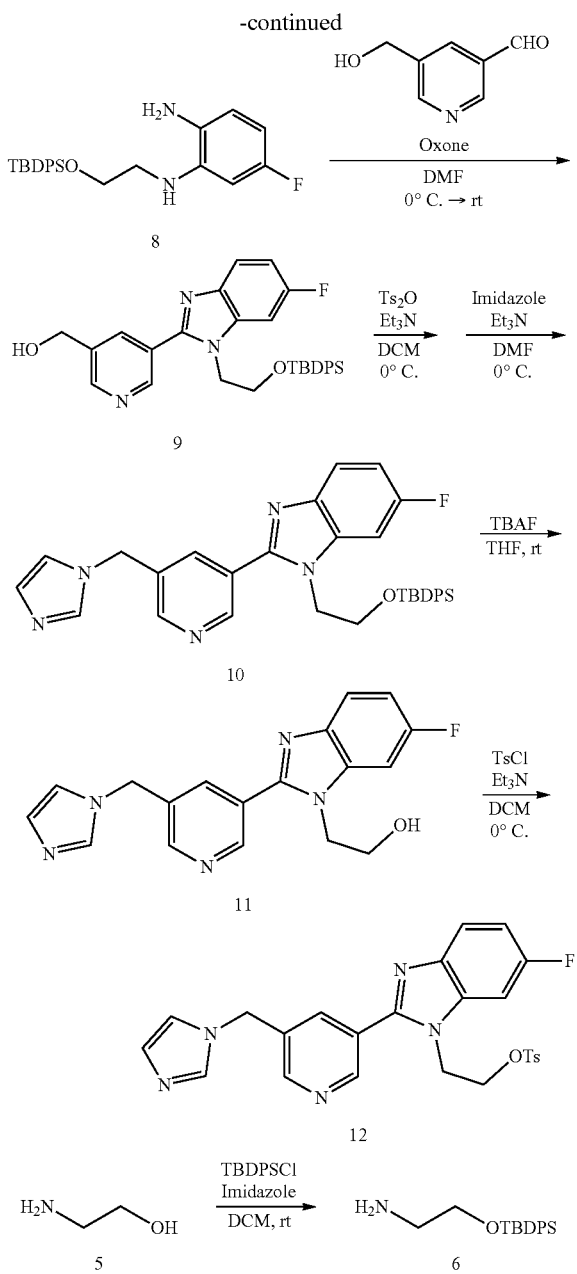

acetate layer was washed with water and a saturated aqueous solution of sodium chloride, and then the washed layer was dried over anhydrous magnesium sulfate and then concentrated under reduced pressure, and the obtained crude product was purified by silica gel chromatography (hexane → hexane/ethyl acetate=10/1) to obtain N-(4,5-difluoro-2-nitrophenyl)-2-(tert-butyldiphenylsilyloxy)ethylamine (Compound 2) (1.72 g, 3.78 mmol).

$^1$H-NMR of Compound 2 (solvent: deuterated chloroform): δ 8.41 (bs, 1H), 8.05 (dd, 1H, $J_{HH}$=8.4, $^3J_{HF}$=10.8 Hz), 7.66-7.64 (m, 4H), 7.44-7.42 (m, 2H), 7.39-7.36 (m, 4H), 6.56 (dd, 1H, $J_{HH}$=6.7, $^3J_{HF}$=12.6 Hz), 3.90 (t, J=5.4 Hz, 2H), 3.40 (dt, J=5.4, 5.4 Hz, 2H), 1.06 (s, 9H).

Synthesis of 5-{5,6-difluoro-1-[2-(tert-butyldiphenylsilyloxy)ethyl]benzimidazol-2-yl}pyridine-3-methanol (Compound 3)

N-(4,5-Difluoro-2-nitrophenyl)-2-(tert-butyldiphenylsilyloxy)ethylamine (Compound 2) (1.72 g, 3.78 mmol) was dissolved in ethyl acetate (25 mL), and then, tin(II) chloride (2.87 g, 15.1 mmol) and water (0.272 mL, 15.1 mmol) were added, and heated under reflux overnight under an argon gas atmosphere. After completion of the reaction, the solvent was distilled off, the obtained crude product was purified by silica gel chromatography (eluent:hexane/ethyl acetate=3/1), the obtained compound was dissolved in N,N'-dimethylformamide (15 mL), and then, 5-hydroxymethyl-3-pyridinecarboxaldehyde (391 mg, 2.85 mmol) and potassium peroxymonosulfate (trade name: Oxone (registered trademark)) (2.10 g, 3.42 mmol) were added at room temperature, and the resultant mixture was stirred at the same temperature for 2 hours under an argon gas atmosphere. After completion of the reaction, into the mixture, a saturated aqueous solution of sodium thiosulfate and a saturated aqueous solution of sodium hydrogen carbonate were added, and extracted three times with ethyl acetate. The combined ethyl acetate layer was washed with water and with a saturated aqueous solution of sodium chloride, the washed layer was dried over anhydrous magnesium sulfate and then concentrated under reduced pressure, and the obtained crude product was purified by silica gel chromatography (eluent: chloroform/methanol=10/1) to obtain 5-{5,6-difluoro-1-[2-(tert-butyldiphenylsilyloxy)ethyl]benzimidazol-2-yl}pyridine-3-methanol (Compound 3) (1080 mg, 1.99 mmol).

$^1$H-NMR of Compound 3 (solvent: deuterated chloroform): δ 8.93 (d, J=2.1 Hz, 1H), 8.72 (d, J=2.1 Hz, 1H), 8.10 (t, J=2.1 Hz, 1H), 7.60 (dd, 1H, $J_{HH}$=8.3, $^3J_{HF}$=10.3 Hz), 7.61-7.36 (m, 6H), 7.30-7.25 (m, 4H), 6.99 (dd, 1H, $J_{HH}$=6.9, $^3J_{HF}$=9.8 Hz), 4.77 (brs, 2H), 4.38 (t, J=5.5 Hz, 2H), 3.93 (t, J=5.5 Hz, 2H), 0.90 (s, 9H).

Synthesis of 2-(p-toluenesulfonyloxymethyl pyridin-3-yl)-5,6-difluoro-1-[2-(tert-butyldiphenylsilyloxy)ethyl]benzimidazole (Compound 4)

5-{5,6-Difluoro-1-[2-(tert-butyldiphenylsilyloxy)ethyl]benzimidazol-2-yl}pyridine-3-methanol (Compound 3) (1080 mg, 1.99 mmol) was dissolved in tetrahydrofuran (20 mL), the atmosphere was replaced with argon gas, and then, triethylamine (333 μL, 2.39 mmol) and p-toluenesulfonic acid anhydride (714 mg, 2.19 mmol) were added at 0° C., and the resultant mixture was stirred at the same temperature for one hour under an argon gas atmosphere. After completion of the reaction, a saturated sodium hydrogen carbonate solution was added, and extracted three times with dichloromethane. The combined dichloromethane layer was con- (Example 3) Synthesis of Compound 102

Compound 102 was synthesized according to the following Scheme 3.

Synthesis of N-(4,5-difluoro-2-nitrophenyl)-2-(tert-butyldiphenylsilyloxy)ethylamine (Compound 2)

2,4,5-Trifluoronitrobenzene (Compound 1) (1.00 g, 5.65 mmol) was dissolved in dichloromethane (25 mL), and the, 2-(tert-butyldiphenylsilyloxy)ethylamine (1.69 g, 5.65 mmol) and potassium carbonate (2.34 g, 17.0 mmol) were added at room temperature, and the resultant mixture was stirred at the same temperature overnight under an argon gas atmosphere. After completion of the reaction, a saturated aqueous solution of ammonium chloride was added, and extracted three times with ethyl acetate. The combined ethyl centrated under reduced pressure, the obtained crude product was purified by silica gel chromatography (eluent: chloroform/methanol=10/1) to obtain 2-(p-toluenesulfonyloxymethyl pyridin-3-yl)-5,6-difluoro-1-[2-(tert-butyldiphenylsilyloxy)ethyl]benzimidazole (Compound 4) (858 mg, 1.23 mmol).

$^1$H-NMR of Compound 4 (solvent: deuterated chloroform): δ 9.01 (d, J=2.1 Hz, 1H), 8.61 (d, J=2.1 Hz, 1H), 8.07 (t, J=2.1 Hz, 1H), 7.81 (d, J=8.3 Hz, 2H), 7.59 (dd, 1H, $J_{HH}$=8.3, $^3J_{HF}$=10.3 Hz), 7.41-7.27 (m, 12H), 6.97 (dd, 1H, $J_{HH}$=6.9, $^3J_{HF}$=9.7 Hz), 5.09 (s, 2H), 4.35 (t, J=5.4 Hz, 2H), 3.94 (t, J=5.4 Hz, 2H), 0.88 (s, 9H).

Synthesis of 2-{5,6-difluoro-2-[5-(imidazol-1-ylmethyl)pyridin-3-yl]benzimidazol-1-yl}ethanol (Compound 5)

Imidazole (127 mg, 1.86 mmol) was dissolved in tetrahydrofuran (10 mL), and then, sodium hydride (74.4 mg, 1.86 mmol) was added at 0° C., and the resultant mixture was stirred at the same temperature for 10 minutes under an argon gas atmosphere. Into the obtained mixture, 2-(p-toluenesulfonyloxymethyl pyridin-3-yl)-5,6-difluoro-1-[2-(tert-butyldiphenylsilyloxy)ethyl]benzimidazole (Compound 4) (858 mg, 1.23 mmol) was added at the same temperature, and the resultant mixture was stirred at the same temperature for 15 minutes under an argon gas atmosphere. After completion of the reaction, water was added, and extracted three times with ethyl acetate. The combined ethyl acetate layer was washed with water, and then the washed layer was dried over anhydrous sodium sulfate and then concentrated under reduced pressure, the obtained crude product was dissolved in 0.2 mL of tetrahydrofuran, and then, tetrabutylammonium fluoride (3.1 mL, tetrahydrofuran solution, around 1 M, 3.1 mmol) was added at 0° C., and the resultant mixture was stirred at room temperature for 15 minutes under an argon gas atmosphere. After completion of the reaction, the reaction solution was concentrated under reduced pressure, and the obtained crude product was purified by silica gel chromatography (dichloromethane/methanol=10/1) to obtain 2-{5,6-difluoro-2-[5-(imidazol-1-ylmethyl)pyridin-3-yl]benzimidazol-1-yl}ethanol (Compound 5) (235 mg, 0.660 mmol).

$^1$H-NMR of Compound 5 (solvent: deuterated chloroform): δ 9.03 (d, J=2.1 Hz, 1H), 8.61 (d, J=2.1 Hz, 1H), 7.91 (t, J=2.1 Hz, 1H), 7.57 (s, 1H), 7.52 (dd, 1H, $J_{HH}$=7.3, $^3J_{HF}$=10.2 Hz), 7.27 (dd, 1H, $J_{HH}$=6.8, $^3J_{HF}$=9.7 Hz), 7.06 (s, 1H), 6.96 (t, J=1.3 Hz, 1H), 5.26 (s, 2H), 4.20 (t, J=5.5 Hz, 2H), 3.98 (t, J=5.5 Hz, 2H), 3.31 (m, 1H).

Synthesis of 5,6-difluoro-2-[5-(imidazol-1-ylmethyl)pyridin-3-yl]-1-[2-(p-toluenesulfonyloxy)ethyl]benzimidazole (Compound 6)

2-{5,6-Difluoro-2-[5-(imidazol-1-ylmethyl)pyridin-3-yl]benzimidazol-1-yl}ethanol (Compound 5) (235 mg, 0.161 mmol) was dissolved in dichloromethane (10.0 mL), and then p-toluenesulfonic acid anhydride (431 mg, 1.32 mmol) and triethylamine (184 μL, 1.32 mmol) were added, and the resultant mixture was stirred at room temperature for 15 minutes under an argon gas atmosphere. After completion of the reaction, a saturated aqueous solution of sodium hydrogen carbonate was added, and extracted three times with dichloromethane. The combined dichloromethane layer was dried and then concentrated under reduced pressure, and the obtained crude product was purified by silica gel chromatography (chloroform/methanol=10/1) to obtain 5,6-difluoro-2-[5-(imidazol-1-ylmethyl)pyridin-3-yl]-1-[2-(p-toluenesulfonyloxy)ethyl]benzimidazole (Compound 6) (129 mg, 0.253 mmol).

$^1$H-NMR of Compound 6 (solvent: deuterated chloroform): δ 8.84 (d, J=2.1 Hz, 1H), 8.64 (d, J=2.1 Hz, 1H), 7.87 (t, J=2.1 Hz, 1H), 7.66 (s, 1H), 7.53 (dd, 1H, $J_{HH}$=7.3, $^3J_{HF}$=10.1 Hz), 7.41 (d, J=8.4 Hz, 2H), 7.14-7.12 (m, 3H), 7.11 (dd, 1H, $J_{HH}$=6.7, $^3J_{HF}$=9.5 Hz), 7.03 (t, J=1.2 Hz, 1H), 5.29 (s, 2H), 4.37 (t, J=5.3 Hz, 2H), 4.23 (t, J=5.3 Hz, 2H), 2.38 (s, 3H).

Synthesis of 5,6-difluoro-1-(2-fluoroethyl)-2-[5-(imidazol-1-ylmethyl)pyridin-3-yl]benzimidazole (Compound 102)

Tetrabutylammonium fluoride (9.8 μL, tetrahydrofuran solution, around 1 M, 9.81 μmol) was concentrated under reduced pressure, and then dissolved in dimethyl sulfoxide (0.2 ml). Into the obtained mixture, 5,6-difluoro-2-[5-(imidazol-1-ylmethyl)pyridin-3-yl]-1-[2-(p-toluenesulfonyloxy)ethyl]benzimidazole (Compound 6) (10.0 mg, 19.6 μmol) was added at room temperature, and the resultant mixture was stirred at room temperature for one hour and at 40° C. overnight under an argon gas atmosphere. After completion of the reaction, water was added, and extracted three times with a mixture solution of ethyl acetate/hexane (1/1). The combined organic layer was dried over anhydrous sodium sulfate and then concentrated under reduced pressure, and the obtained crude product was purified by HPLC under the following conditions to obtain 5,6-difluoro-1-(2-fluoroethyl)-2-[5-(imidazol-1-ylmethyl)pyridin-3-yl]benzimidazole (Compound 102) (1.2 mg, 3.36 μmol).

$^1$H-NMR of Compound 102 (solvent: deuterated chloroform): δ 8.92 (d, J=1.9 Hz, 1H), 8.65 (d, J=1.9 Hz, 1H), 7.83 (s, 1H), 7.71-7.47 (m, 3H), 7.16 (s, 1H), 6.97 (s, 1H), 5.28 (s, 2H), 4.20 (dt, J=47, 4.7 Hz, 2H), 3.98 (dt, J=26, 4.7 Hz, 2H).

HPLC Conditions

Column: Xbridge Phenyl 10 μm (trade name, manufactured by Waters Corporation, size: 10×250 mm)
Mobile phase A: 10 mM ammonium bicarbonate solution
Mobile phase B: methanol
Transfer of mobile phase: change the mixture ratio of each of mobile phases A and B as shown in the following Table 1 to control the concentration gradient.

TABLE 1

| Time after injection (minutes) | Mobile phase A (vol %) | Mobile phase B (vol %) |
| --- | --- | --- |
| 0.0 to 10.0 | 80 → 65 | 20 → 35 |
| 10.0 to 25.0 | 65 → 50 | 35 → 50 |
| 25.0 to 25.1 | 50 → 80 | 50 → 20 |
| 25.1 to 35.0 | 80 | 20 |

Flow rate: 4.0 mL/min
Detector: ultraviolet-visible absorption photometer (detection wavelength: 293 nm)

(Example 4) Synthesis of Compound [$^{18}$F]102

[$^{18}$F] Fluoride ion-containing H$_2$$^{18}$O (the amount of radioactivity: 4540 MBq, correction value at the start of synthesis) was allowed to pass through a Sep-Pak column (trade name: Sep-Pak (registered trademark) Light Cartridge Accell (registered trademark) Plus QMA Carbonate, manufactured by Waters Corporation, the amount of filler: 130 mg), and [$^{18}$F] fluoride ions were adsorbed and collected on the column. A potassium carbonate aqueous solution (42.4 μmol/L, 0.3 mL) and a solution (0.7 mL) of Kryptofix 222 (trade name, manufactured by Merck KGaA) (14 mg, 37.2 μmol) in acetonitrile were allowed to pass through the column to elute the [$^{18}$F] fluoride ions. The obtained eluate was heated to 110° C. under an argon gas flow to evaporate water, and then acetonitrile (0.5 mL×2) was added thereto, and the resultant mixture was azeotropically evaporated to dryness. To the obtained product, an acetonitrile/dimethyl sulfoxide (9:1) mixture (1.0 mL) in which 5,6-difluoro-2-[5-(imidazol-1-ylmethyl)pyridin-3-yl]-1-[2-(p-toluenesulfonyloxy)ethyl]benzimidazole (Compound 6) (5 mg, 0.00981 mmol) had been dissolved was added, and the resultant mixture was heated at 100° C. for 5 minutes. After completion of the reaction, into the mixture, water for injection (2.0 mL) was added, and the fraction of 5,6-difluoro-1-(2-[$^{18}$F]fluoroethyl)-2-[5-(imidazol-1-ylmethyl)pyridin-3-yl]benzimidazole (Compound [$^{18}$F]102) was separated by HPLC under the following conditions.

HPLC Conditions

Column: Develosil RPAQUEOUS (trade name, manufactured by Nomura Chemical Co., Ltd., size: 10×250 mm)
Mobile phase: 10 mM ammonium bicarbonate solution/acetonitrile=65/35
Flow rate: 4.0 mL/min
Detector: ultraviolet-visible absorption photometer (detection wavelength: 254 nm)
A liquid obtained by adding 10 mL of water to the fraction was allowed to pass through a Sep-Pak C18 column (trade name: Sep-Pak (registered trademark) Light C18 Cartridges, manufactured by Waters Corporation, the amount of filler: 130 mg), and 5,6-difluoro-1-(2-[$^{18}$F]fluoroethyl)-2-[5-(imidazol-1-ylmethyl)pyridin-3-yl]benzimidazole (Compound [$^{18}$F]102) was adsorbed and collected on the column. The column was washed with 5 mL of water, and then 1 mL of ethanol was allowed to pass through the column, and an ethanol solution of 5,6-difluoro-1-(2-[$^{18}$F]fluoroethyl)-2-[5-(imidazol-1-ylmethyl)pyridin-3-yl]benzimidazole (Compound [$^{18}$F]102) was obtained. The amount of the obtained radioactivity was 789 MBq immediately after the synthesis (61 minutes after the start of the synthesis). Further, when the TLC analysis was conducted under the following conditions, the radiochemical purity was 99.1%.

TLC Analysis Conditions

TLC plate: Silica Gel 60 $F_{254}$ (product name, manufactured by Merck KGaA)
Development phase: acetonitrile/water/diethylamine=10/1/1
RI detector: Rita Star, manufactured by Raytest GmbH

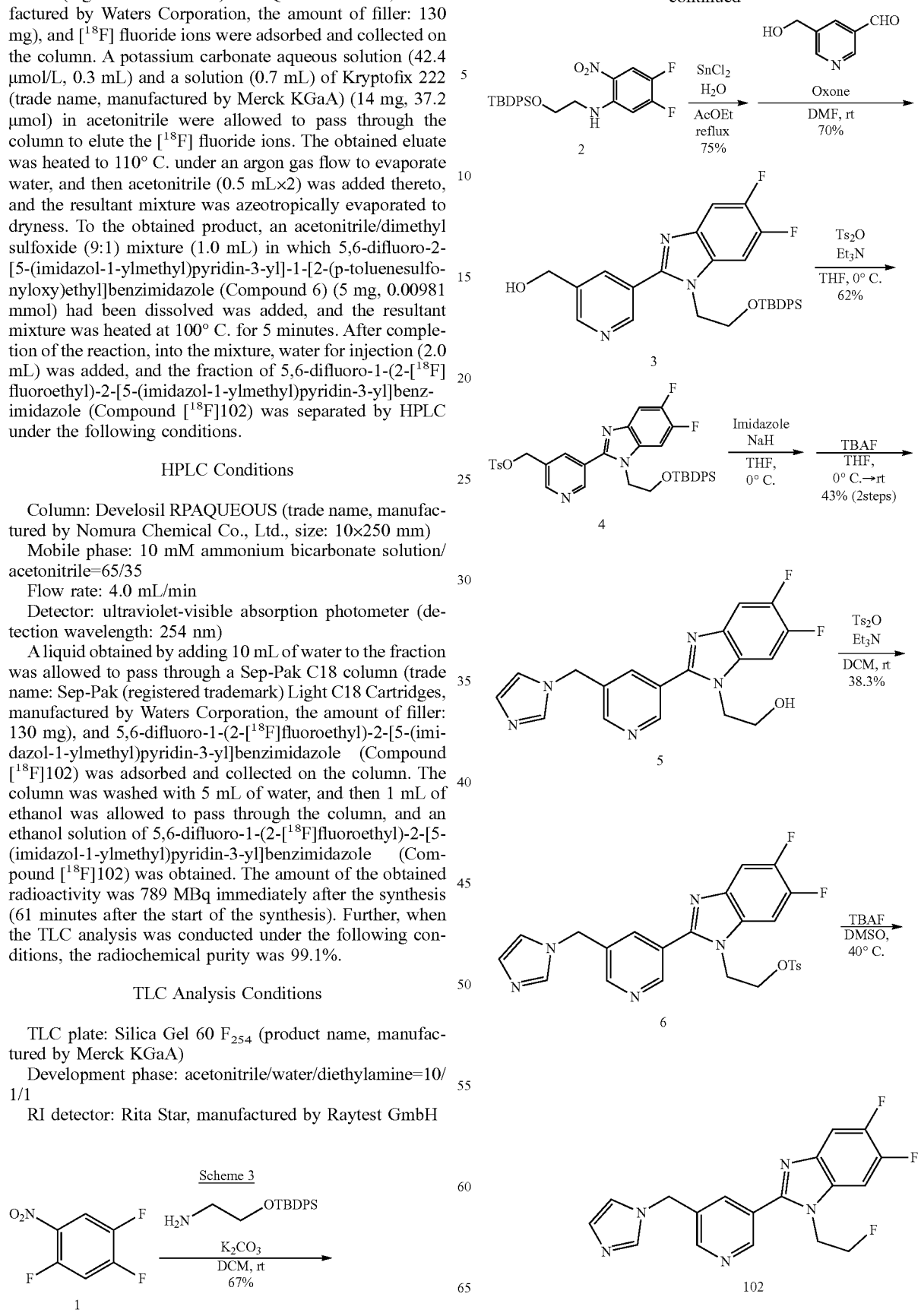

(Example 5) Synthesis of Compound 103

Compound 103 was synthesized according to the following Scheme 4.

Synthesis of 2-(tert-butyldiphenylsilyloxy)ethylamine (Compound 2)

2-Aminoethanol (Compound 1) (2.2 mL, 40.0 mmol) was dissolved in dichloromethane (100 mL), and then, tert-butyldiphenylsilyl chloride (15.6 mL, 60.0 mmol) and imidazole (5.44 g, 80.0 mmol) were added under room temperature, and the resultant mixture was stirred at room temperature overnight under an argon gas atmosphere. After completion of the reaction, water was added under ice cooling, and then extracted three times with dichloromethane. The combined dichloromethane layer was dried over anhydrous sodium sulfate and then concentrated under reduced pressure to obtain a crude product, and the crude product was purified by silica gel chromatography (eluent: ethyl acetate/methanol=100/0→10/1→5/1) to obtain 2-(tert-butyldiphenylsilyloxy)ethylamine (Compound 2) (12.2 g, 40.7 mmol).

$^1$H-NMR of Compound 2 (solvent: deuterated chloroform): δ 7.67-7.65 (m, 4H), 7.44-7.36 (m, 6H), 3.70 (t, J=5.3 Hz, 2H), 2.84 (t, J=5.3 Hz, H), 2.79 (br, 2H), 3.08 (br, 2H), 1.07 (s, 9H).

Synthesis of 2,5-difluoro-4-nitrobenzonitrile (Compound 4)

1-Bromo-2,5-difluorobenzene (Compound 3) (0.440 mL, 4.00 mmol) was dissolved in sulfuric acid (5.00 mL), and then, potassium nitrate (445 mg, 4.40 mmol) was added under ice cooling, and the resultant mixture was stirred at room temperature for one hour under an argon gas atmosphere. After completion of the reaction, water was added, and extracted three times with dichloromethane. The combined dichloromethane layer was dried over anhydrous sodium sulfate and then concentrated under reduced pressure to obtain a crude product. The obtained crude product (952 mg, 4.00 mmol) was dissolved in N-methylpyrrolidone (6.00 mL), and then into the obtained mixture, copper cyanide (565 mg, 6.32 mmol) was added at room temperature, and the resultant mixture was stirred at room temperature for 7 hours under an argon gas atmosphere. After completion of the reaction, sodium sulfate and water were added, and extracted three times with diethyl ether. The combined diethyl ether layer was dried over anhydrous sodium sulfate and then concentrated under reduced pressure to obtain 2,5-difluoro-4-nitrobenzonitrile (Compound 4) (541 mg, 2.94 mmol).

Synthesis of 5-{[2-(tert-butyldiphenylsilyloxy)ethyl]amino}-2-fluoro-4-nitrobenzonitrile (Compound 5)

2,5-Difluoro-4-nitro benzonitrile (Compound 4) (0.541 g, 2.94 mmol) was dissolved in dichloromethane (20 mL), and then, 2-(tert-butyldiphenylsilyloxy)ethylamine (Compound 2) (2.04 g, 6.82 mmol) and potassium carbonate (1.57 g, 11.4 mmol) were added at room temperature, and the resultant mixture was stirred at room temperature for 13 hours under an argon gas atmosphere. After completion of the reaction, water was added, and extracted twice with dichloromethane. The combined dichloromethane layer was dried over anhydrous sodium sulfate and then concentrated under reduced pressure, and the obtained crude product was purified by silica gel chromatography (hexane/ethyl acetate =10/1) to obtain 5-{[2-(tert-butyldiphenylsilyloxy)ethyl]amino}-2-fluoro-4-nitrobenzonitrile (Compound 5) (1.08 g, 2.33 mmol).

$^1$H-NMR of Compound 5 (solvent: deuterated chloroform): δ 8.21 (br, 1H), 8.03 (d, J=9.1 Hz, 1H), 7.64 (dd, J=8.1, 1.4 Hz, 4H), 7.46-7.41 (m, 2H), 7.40-7.36 (m, 4H), 7.09 (d, J=5.2 Hz, 1H), 3.92 (t, J=5.2 Hz, 2H), 3.41 (dd, J=10.7, 5.2 Hz, 2H), 1.07 (s, 9H).

Synthesis of 4-amino-5-{[2-(tert-butyldiphenylsilyloxy)ethyl]amino}-2-fluorobenzonitrile (Compound 6)

5-{[2-(tert-Butyldiphenylsilyloxy)ethyl]amino}-2-fluoro-4-nitrobenzonitrile (Compound 5) (1.08 g, 2.33 mmol) was dissolved in ethyl acetate (8.0 mL), and then, tin(II) chloride (1.77 g, 9.32 mmol) and water (0.17 mL, 9.32 mmol) were added, and heated under reflux for one hour under an argon gas atmosphere. After completion of the reaction, a 4 N sodium hydroxide aqueous solution was added, and extracted twice with ethyl acetate. The combined ethyl acetate layer was dried over anhydrous sodium sulfate and then concentrated under reduced pressure, and the obtained crude product was purified by silica gel chromatography (hexane/ethyl acetate=5/1) to obtain 4-amino-5-{[2-(tert-butyldiphenylsilyloxy)ethyl]amino}-2-fluorobenzonitrile (Compound 6) (670 mg, 1.55 mmol).

$^1$H-NMR of Compound 6 (solvent: deuterated chloroform): δ 7.67-7.65 (m, 4H), 7.47-7.43 (m, 2H), 7.41-7.37 (m, 4H), 6.67 (d, J=6.1 Hz, 1H), 6.44 (d, J=10.2 Hz, 1H), 4.03 (s, 2H), 3.92 (t, J=5.1 Hz, 2H), 3.43 (t, J =5.7 Hz, 1H), 3.13 (dd, J=10.5, 5.8 Hz, 2H), 1.08 (s, 9H).

Synthesis of 1-[2-(tert-butyldiphenylsilyloxy)ethyl]-5-fluoro-2-[5-(hydroxymethyl)pyridin-3-yl]-1H-benzo[d]imidazole-6-carbonitrile (Compound 7)

5-Hydroxymethyl-3-pyridinecarboxaldehyde (212 mg, 1.55 mmol) was dissolved in N,N'-dimethylformamide (6 mL), and then, under ice cooling, 4-amino-5-{[2-(tert-butyldiphenylsilyloxy)ethyl]amino}-2-fluorobenzonitrile (Compound 6) (670 mg, 1.55 mmol) and potassium peroxymonosulfate (trade name: Oxone (registered trademark)) (1.14 g, 1.86 mmol) were added, and the resultant mixture was stirred at room temperature for 2 hours under an argon gas atmosphere. After completion of the reaction, a saturated aqueous solution of sodium thiosulfate and a saturated aqueous solution of sodium hydrogen carbonate were added at 0° C., and then extracted three times with ethyl acetate. The combined ethyl acetate layer was dried over anhydrous sodium sulfate and then concentrated under reduced pressure, and the obtained crude product was purified by silica gel chromatography (ethyl acetate/hexane/methanol=10/5/1) to obtain 1-[2-(tert-butyldiphenylsilyloxy)ethyl]-5-fluoro-2-[5-(hydroxymethyl)pyridin-3-yl]-1H-benzo[d]imidazole-6-carbonitrile (Compound 7) (853 mg, 1.55 mmol).

$^1$H-NMR of Compound 7 (solvent: deuterated chloroform): δ 8.94 (d, J=2.1 Hz, 1H), 8.76 (d, J=2.1 Hz, 1H), 8.14 (t, J=2.1 Hz, 1H), 7.59 (d, J=9.2 Hz, 1H), 7.44-7.41 (m, 3H), 7.37-7.35 (m, 4H), 7.32-7.29 (m, 4H), 4.79 (s, 2H), 4.42 (t, J=5.5 Hz, 2H), 3.96 (t, J=5.5 Hz, 2H) , 0.91 (s, 9H).

Synthesis of 2-[5-(1H-imidazol-1-ylmethyl)pyridin-3-yl]-1-[2-(tert-butyldiphenylsilyloxy)ethyl]-5-fluoro-1H-benzo[d]imidazole-6-carbonitrile (Compound 8)

1-[2-(tert-Butyldiphenylsilyloxy)ethyl]-5-fluoro-2-[5-(hydroxymethyl)pyridin-3-yl]-1H-benzo[d]imidazole-6- carbonitrile (Compound 7) (853 mg, 1.55 mmol) was dissolved in dichloromethane (15 mL), and then, under ice cooling, triethylamine (0.65 mL, 4.65 mmol) and p-toluenesulfonic acid anhydride (1.01 g, 3.10 mmol) were added, and the resultant mixture was stirred at room temperature for 15 minutes under an argon gas atmosphere. After completion of the reaction, water was added, and extracted twice with dichloromethane. The combined dichloromethane layer was dried over anhydrous sodium sulfate and then concentrated under reduced pressure to obtain a crude product. Into a solution obtained by dissolving imidazole (527 mg, 7.75 mmol) in N,N'-dimethylformamide (5 mL), triethylamine (1.08 mL, 7.75 mmol) was added under ice cooling, and then into the obtained mixture, the previously obtained crude product that had been dissolved in N,N'-dimethylformamide (5 mL) was added, and the resultant mixture was stirred at room temperature for 17 hours under an argon gas atmosphere. After completion of the reaction, water was added, and extracted three times with ethyl acetate. The combined ethyl acetate layer was dried over anhydrous sodium sulfate and then concentrated under reduced pressure, and the obtained crude product was purified by silica gel chromatography (dichloromethane/methanol=30/1) to obtain 2-[5-(1H-imidazol-1-ylmethyl)pyridin-3-yl]-1-[2-(tert-butyldiphenylsilyloxy)ethyl]-5-fluoro-1H-benzo[d]imidazole-6-carbonitrile (Compound 8) (311 mg, 0.518 mmol).

$^1$H-NMR of Compound 8 (solvent: deuterated chloroform): δ 9.07 (d, J=2.1 Hz, 1H), 8.63 (d, J=2.2 Hz, 1H), 7.90 (t, J=2.1 Hz, 1H), 7.58 (d, J=9.2 Hz, 1H), 7.56 (s, 1H), 7.45-7.41 (m, 2H), 7.39 (d, J=5.2 Hz, 1H), 7.36-7.34 (m, 4H), 7.31-7.28 (m, 4H), 7.11 (t, J=1.0 Hz, 1H), 6.89 (t, J=1.3 Hz, 1H), 5.18 (s, 2H), 4.36 (t, J=5.5 Hz, 2H), 3.96 (t, J=5.4 Hz, 2H), 0.91 (s, 9H).

Synthesis of 2-[5-(1H-imidazol-1-ylmethyl)pyridin-3-yl]-5-fluoro-1-(2-hydroxyethyl)-1H-benzo[d]imidazole-6-carbonitrile (Compound 9)

2-[5-(1H-Imidazol-1-ylmethyl) pyridin-3-yl]-1-[2-(tert-butyldiphenylsilyloxy)ethyl]-5-fluoro-1H-benzo[d]imidazole-6-carbonitrile (Compound 8) (311 mg, 0.518 mmol) was dissolved in tetrahydrofuran (5 mL), and then, under ice cooling, tetrabutylammonium fluoride (1 mol/L tetrahydrofuran solution) (0.78 mL, 0.78 mmol) was added, and the resultant mixture was stirred at room temperature for 20 minutes under an argon gas atmosphere. After completion of the reaction, the reaction solution was concentrated under reduced pressure, and the obtained crude product was purified by silica gel chromatography (dichloromethane/methanol=10/1→5/1) to obtain 2-[5-(1H-imidazol-1-ylmethyl) pyridin-3-yl]-5-fluoro-1-(2-hydroxyethyl)-1H-benzo[d] imidazole-6-carbonitrile (Compound 9) (167 mg, 0.461 mmol).

$^1$H-NMR of Compound 9 (solvent: deuterated chloroform): δ 9.08 (d, J=1.9 Hz, 1H), 8.71 (d, J=2.2 Hz, 1H), 7.87 (s, 1H), 7.76 (d, J=9.4 Hz, 1H), 7.64 (s, 1H), 7.59 (d, J=9.3 Hz, 1H), 7.15 (s, 1H), 6.98 (s, 1H), 5.31 (s, 2H), 4.26 (t, J=5.4 Hz, 2H), 4.03 (d, J=5.3 Hz, 2H).

Synthesis of 2-{2-[5-(1H-imidazol-1-ylmethyl)pyridin-3-yl]-6-cyano-5-fluoro-1H-benzo[d]imidazol-1-yl}ethyl-4-methylbenzenesulfonate (Compound 10)

2-[5-(1H-Imidazol-1-ylmethyl)pyridin-3-yl]-5-fluoro-1-(2-hydroxyethyl)-1H-benzo[d]imidazole-6-carbonitrile (Compound 9) (50.0 mg, 0.138 mmol) was dissolved in dichloromethane (1.5 mL), and then, under ice cooling, triethylamine (58.5 μL, 0.420 mmol) and p-toluenesulfonic acid anhydride (91.4 mg, 0.280 mmol) were added, and the resultant mixture was stirred at room temperature for one hour under an argon gas atmosphere. After completion of the reaction, the reaction solution was purified by silica gel chromatography (dichloromethane/methanol=20/1→10/1) to obtain 2-{2-[5-(1H-imidazol-1-ylmethyl)pyridin-3-yl]-6-cyano-5-fluoro-1H-benzo[d]imidazol-1-yl}ethyl-4-methylbenzenesulfonate (Compound 10) (13.9 mg, 0.0269 mmol).

$^1$H-NMR of Compound 10 (solvent: deuterated chloroform): δ 8.88 (d, J=2.1 Hz, 1H), 8.69 (d, J=2.1 Hz, 1H), 7.92 (t, J=2.1 Hz, 1H), 7.78 (d, J=8.2 Hz, 2H), 7.70 (s, 1H), 7.56 (d, J=9.0 Hz, 1H), 7.43 (d, J=8.5 Hz, 2H), 7.17 (d, J=8.0 Hz, 2H), 7.03 (s, 1H), 5.32 (s, 2H), 4.45 (t, J=5.1 Hz, 2H), 4.26 (t, J=5.1 Hz, 2H), 2.40 (s, 3H).

Synthesis of 2-[5-(1H-imidazol-1-ylmethyl)pyridin-3-yl]-5-fluoro-1-(2-fluoroethyl)-1H-benzo[d]imidazole-6-carbonitrile (Compound 103)

2-[5-(1H-Imidazol-1-ylmethyl)pyridin-3-yl]-5-fluoro-1-(2-hydroxymethyl)-1H-benzo[d]imidazole-6-carbonitrile (Compound 10) (10.0 mg, 0.0194 mmol) was dissolved in dichloromethane (2 mL), and then N,N-diethylaminosulfur trifluoride (10.9 μL, 0.0831 mmol) was added at room temperature, and the resultant mixture was stirred at the same temperature for 30 minutes under an argon gas atmosphere. After completion of the reaction, a saturated aqueous solution of sodium hydrogen carbonate was added, the obtained mixture was further stirred for one hour, and then extracted three times with chloroform. The combined chloroform layer was washed with water, and then the washed layer was dried over anhydrous magnesium sulfate and then concentrated under reduced pressure, and the obtained crude product was purified by silica gel chromatography (hexane→hexane/ethyl acetate=10/1) to obtain 2-[5-(1H-imidazol-1-ylmethyl)pyridin-3-yl]-5-fluoro-1-(2-fluoroethyl)-1H-benzo[d]imidazole-6-carbonitrile (Compound 103) (1.6 mg, 0.00439 mmol).

$^1$H-NMR of Compound 103 (solvent: deuterated chloroform): δ 8.95 (d, J=2.1 Hz, 1H), 8.70 (d, J=2.1 Hz, 1H), 7.83 (t, J=2.1 Hz, 1H), 7.72 (d, J=5.2 Hz, 1H), 7.63-7.61 (m, 2H), 7.16 (s, 1H), 6.97 (s, 1H), 5.29 (s, 2H), 4.78 (dt, 1H, $J_{HH}$=4.6, $^2J_{HF}$=46.7 Hz), 4.47 (dt, 1H, $J_{HH}$=4.6, $^3J_{HF}$=25.5 Hz).

$^{19}$F-NMR (solvent: deuterated chloroform, resonance frequency: 470 MHz): δ −113.7 (t, $^3J_{HF}$=7.2 Hz), −219.3 (dd, $^2J_{HF}$=46.7 Hz, $^3J_{HF}$=25.5 Hz).

(Example 6) Synthesis of Compound [$^{18}$F]103

[$^{18}$F] Fluoride ion-containing $H_2^{18}O$ (the amount of radioactivity: 2470 MBq, correction value at the start of synthesis) was allowed to pass through a Sep-Pak column (trade name: Sep-Pak (registered trademark) Light Cartridge Accell (registered trademark) Plus QMA Carbonate, manufactured by Waters Corporation, the amount of filler: 130 mg), and [$^{18}$F] fluoride ions were adsorbed and collected on the column. A potassium carbonate aqueous solution (42.4 μmol/L, 0.3 mL) and a solution (0.7 mL) of Kryptofix 222 (trade name, manufactured by Merck KGaA) (14 mg, 37.2 μmol) in acetonitrile were allowed to pass through the column to elute the [$^{18}$F] fluoride ions. The obtained eluate was heated to 110° C. under an argon gas flow to evaporate water, and then acetonitrile (0.5 mL×2) was added thereto, and the resultant mixture was azeotropically evaporated to dryness. To the obtained product, an acetonitrile/dimethyl sulfoxide (9:1) mixture (1.0 mL) in which 2-{2-[5-(1H-imidazol-1-ylmethyl)pyridin-3-yl]-6-cyano-5-fluoro-1H-benzo[d]imidazol-1-yl}ethyl-4-methylbenzenesulfonate (Compound 10) (5 mg, 0.00968 mmol) had been dissolved was added, and the resultant mixture was heated at 100° C. for 5 minutes. After completion of the reaction, into the mixture, water for injection (2.0 mL) was added, and the fraction of 2-[5-(1H-imidazol-1-ylmethyl)pyridin-3-yl]-5-fluoro-1-(2-[$^{18}$F]fluoroethyl)-1H-benzo[d]imidazole-6-carbonitrile (Compound [$^{18}$F]103) was separated by HPLC under the following conditions.

HPLC Conditions

Column: Develosil RPAQUEOUS (trade name, manufactured by Nomura Chemical Co., Ltd., size: 10×250 mm)
Mobile phase: 10 mM ammonium bicarbonate solution/acetonitrile=75/25
Flow rate: 4.0 mL/min
Detector: ultraviolet-visible absorption photometer (detection wavelength: 254 nm)
A liquid obtained by adding 10 mL of water to the fraction was allowed to pass through a Sep-Pak C18 column (trade name: Sep-Pak (registered trademark) Light C18 Cartridges, manufactured by Waters Corporation, the amount of filler: 130 mg), and 2-[5-(1H-imidazol-1-ylmethyl)pyridin-3-yl]-5-fluoro-1-(2-[$^{18}$F]fluoroethyl)-1H-benzo[d]imidazole-6-carbonitrile (Compound [$^{18}$F]103) was adsorbed and collected on the column. The column was washed with 5 mL of water, and then 1 mL of ethanol was allowed to pass through the column to elute 2-[5-(1H-imidazol-1-ylmethyl)pyridin-3-yl]-5-fluoro-1-(2-[$^{18}$F]fluoroethyl)-1H-benzo[d]imidazole-6-carbonitrile (Compound [$^{18}$F]103), and an ethanol solution of 2-[5-(1H-imidazol-1-ylmethyl)pyridin-3-yl]-5-fluoro-1-(2-[$^{18}$F]fluoroethyl)-1H-benzo[d]imidazole-6-carbonitrile (Compound [$^{18}$F]103) was obtained. The amount of the obtained radioactivity was 795 MBq immediately after the synthesis (82 minutes after the start of the synthesis). Further, when the TLC analysis was conducted under the following conditions, the radiochemical purity was 98.7%.

TLC Analysis Conditions

TLC plate: Silica Gel 60 $F_{254}$ (product name, manufactured by Merck KGaA)
Development phase: acetonitrile/water/diethylamine=10/1/1
RI detector: Rita Star, manufactured by Raytest GmbH Scheme 4

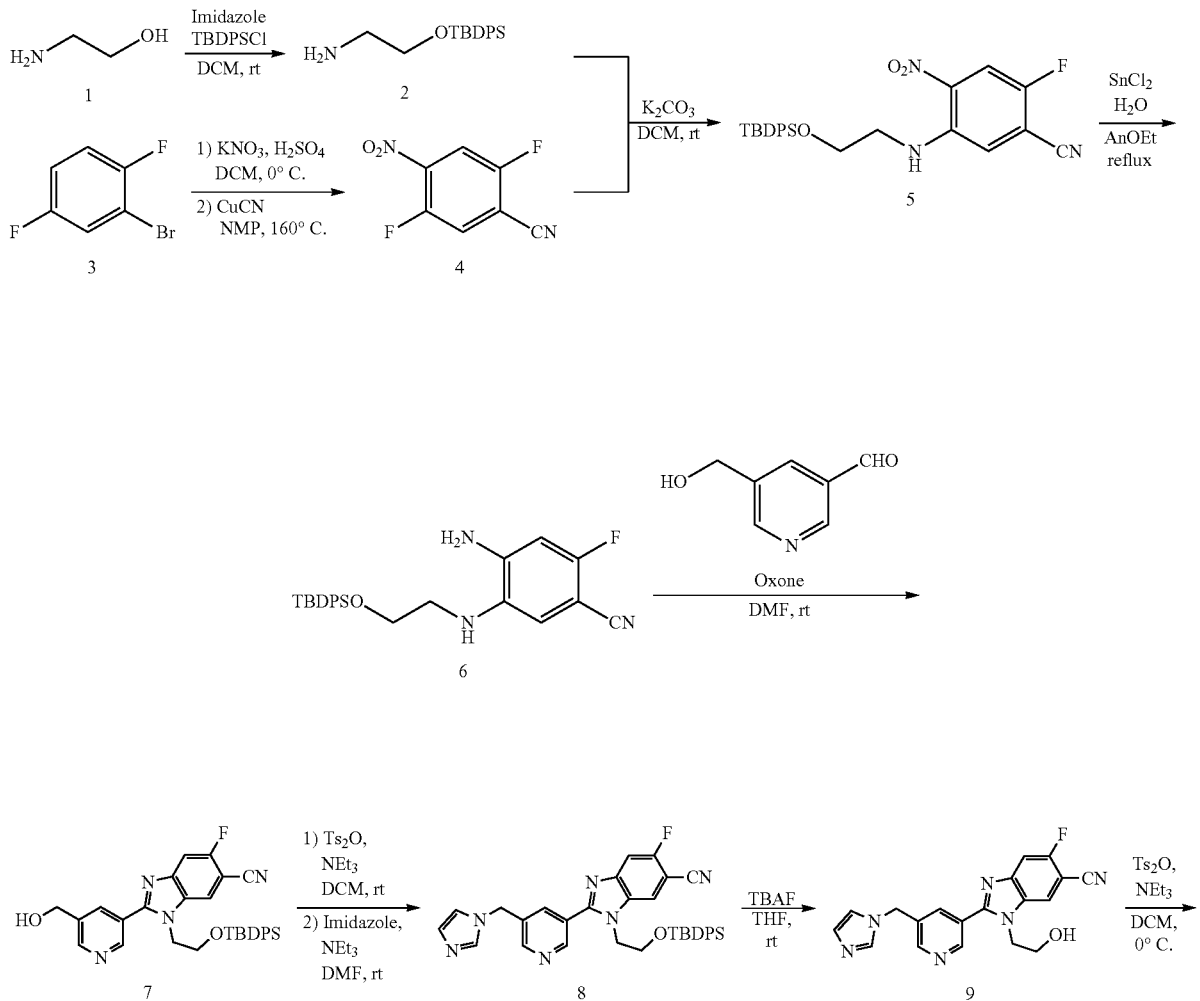

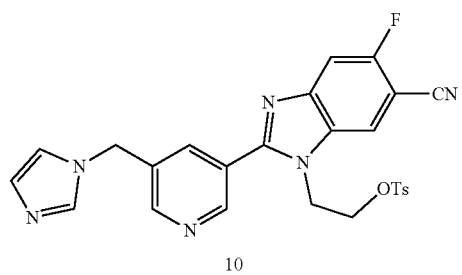
10

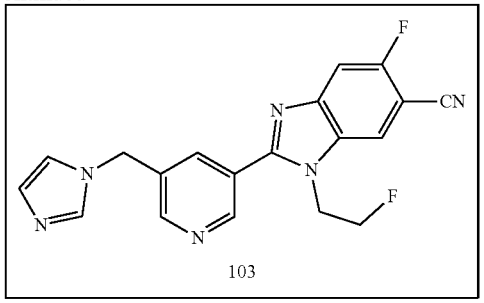
103

Evaluation 1: In Vitro Autoradiography Using Human Adrenal Tumor

By using a frozen human adrenal tissue specimen containing a lesion region having an aldosterone-producing tumor site, and a normal region in an adjacent part to the lesion region, in vitro autoradiography was performed. Specifically, a slide glass on which a section prepared by embedding the specimen in an embedding medium for preparing a frozen tissue section (Tissue-Tek O.C.T. Compound, manufactured by Sakura Finetek Japan Co., Ltd.), and thinly cutting the embedded specimen of human adrenal tissue to have a thickness of 7 μm had been pasted (stored at −80° C., hereinafter, referred to as human adrenal section) was used for experiment.

A solution of each of Compounds [$^{18}$F]100, [$^{18}$F]101, [$^{18}$F]102, and [$^{123}$I]103, which had been obtained in Reference Example 2, Example 2, 4, or 6, and Compound [$^{123}$I]IMTO (reference compound) was dispensed into a vial, and the amount of radioactivity was measured by a radioisotope dose calibrator (CRC-15R, manufactured by Capintec, Inc.) The radioactive concentration of a solution that had been prepared by adding each solution obtained above to human plasma (hereinafter referred to as reaction mixture) was measured by using an autowell gamma system (ARC-7001, manufactured by Hitachi, Ltd.).

For preincubation, a human adrenal section was immersed in phosphate-buffered saline (PBS) at 37° C. for 5 minutes, and then immersed in human plasma at 37° C. for 5 minutes. Next, as a reaction step, the human adrenal section was immersed in the reaction mixture at 37° C. for 10 minutes. After that, the human adrenal section was washed with human plasma five times at 37° C. for 2 minutes, and then air-dried. Further, a piece of filter paper, which had been cut out into a circular shape and had been pasted on a slide glass, was impregnated with a known amount of the reaction mixture, and then air dried, and the resultant piece was used as a standard radiation source.

The air-dried human adrenal section and the air-dried standard radiation source were exposed to an imaging plate (BAS-SR2040, manufactured by Fujifilm Corporation) (IP sheet), and autoradiograms were obtained by a fluoro image analyzer (Typhoo FLA 7000 IP, manufactured by GE Healthcare Japan Corporation). A region of interest (ROI) was set in each of the lesion region and normal region obtained on the autoradiograms, and the radiation count was determined. The ROI was also set for the standard radiation source, and the radiation count was determined.

For the autoradiograms obtained for the human adrenal section, the radiation count (correction value) of each region (lesion region or normal region) was determined as in formula (1) as a correction value to the standard radiation source.

$$\text{Radiation count (correction value) of each region} = \frac{\text{Radiation count of each region}}{\text{Radiation count of standard radiation source}} \quad (1)$$

The binding ability of the compound according to the present invention (each of Compounds [$^{18}$F]101, [$^{18}$F]102, and [$^{18}$F]103) to each region (lesion region or normal region) was determined as in formulas (2) and (3) as the relative value in a case where the radiation count (correction value) in each region of [$^{123}$I]IMTO (reference compound) was set to 1. Further, the lesion/normal ratio was determined as in formula (4).

$$\text{Binding ability of lesion region} = \frac{\text{Radiation count (correction value) in lesion region of the compound according to the present invention}}{\text{Radiation count (correction value) in lesion region of }[^{123}I]IMTO} \quad (2)$$

$$\text{Binding ability of normal region} = \frac{\text{Radiation count (correction value) in normal region of the compound according to the present invention}}{\text{Radiation count (correction value) in normal region of }[^{123}I]IMTO} \quad (3)$$

$$\text{Lesion/normal ratio} = \frac{\text{Binding ability of lesion region}}{\text{Binding ability of normal region}} \quad (4)$$

The obtained results are shown in FIG. 1 and Table 2. As is apparent from FIG. 1, the compounds according to the present invention (Compounds [$^{18}$F]101, [$^{18}$F]102, and [$^{18}$F]103) each showed the lesion sites (Samples 1 to 6) with higher concentration than that of Compound [$^{18}$F]100 (Reference Example 2), and it was indicated that the compounds according to the present invention were highly accumulative at the lesion sites. In addition, as shown in Table 2, the compounds according to the present invention each had values of the binding ability (B2) to lesion regions higher than those of the conventional Compound [$^{18}$F]100 (Reference Example 2), also had lesion/normal ratios (B2/B1) equivalent to or higher than those of the conventional Compound [$^{18}$F]100 (Reference Example 2), and it was indicated that the compounds according to the present invention are highly accumulative and have high binding specificity to the lesion site.

TABLE 2

| | Compound [¹⁸F]100 (control) | | | Compound [¹⁸F]101 | | | Compound [¹⁸F]102 | | | Compound [¹⁸F]103 | | |
|---|---|---|---|---|---|---|---|---|---|---|---|---|
| | Binding ability ratio to reference compound | | | Binding ability ratio to reference compound | | | Binding ability ratio to reference compound | | | Binding ability ratio to reference compound | | |
| Sample | B2 | B1 | B2/B1 | B2 | B1 | B2/B1 | B2 | B1 | B2/B1 | B2 | B1 | B2/B1 |
| 1 | 0.14 | 0.01 | 5.68 | 0.19 | 0.00 | 14.44 | 0.19 | 0.01 | 6.78 | 0.23 | 0.02 | 4.57 |
| 2 | 0.23 | 0.02 | 9.31 | 0.24 | 0.01 | 19.66 | 0.31 | 0.03 | 8.69 | 0.46 | 0.04 | 12.05 |
| 3 | 0.23 | 0.02 | 7.19 | 0.32 | 0.03 | 8.44 | 0.65 | 0.05 | 8.20 | 0.79 | 0.20 | 2.68 |
| 4 | 0.11 | 0.01 | 4.19 | 0.21 | 0.01 | 8.28 | 0.41 | 0.05 | 4.32 | 0.33 | 0.08 | 2.03 |
| 5 | 0.08 | 0.01 | 7.83 | 0.13 | 0.01 | 14.94 | 0.14 | 0.01 | 9.21 | 0.29 | 0.04 | 5.17 |
| 6 | 0.32 | 0.01 | 32.86 | 0.45 | 0.01 | 37.80 | 0.63 | 0.03 | 23.93 | 1.09 | 0.07 | 15.42 |

※ In Table 2, B2 indicates the binding ability to a lesion region, B1 indicates the binding ability to a normal region, and B2/B1 indicates the lesion/normal ratio.

Evaluation 2: Pharmacokinetic Distribution Experiment

The compounds according to the present invention (Compounds [¹⁸F]101, [¹⁸F]102, and [¹⁸F]103) were administered to three normal rats without anesthesia. Imaging data for 15 minutes under isoflurane anesthesia were collected at 60 minutes and 180 minutes after the administration. The imaging data were subjected to image reconstruction by a positron emission tomography (PET) device (instrument: eXplore VISTA, manufactured by GE Healthcare Japan Corporation), and then a volume of interest (VOI) was set in each of the liver, kidney, and spleen, and a standardized uptake value (SUV) of each tissue was determined as in formula (5). The results are shown in FIG. 2.

$$\text{Standardized uptake value } (SUV) \text{ of each tissue} = \frac{\text{Radioactive concentration of } VOI \text{ of each tissue}}{\text{Administered radioactivity/Body weight of rat}} \quad (5)$$

As shown in FIG. 2, the Compounds [¹⁸F]101, [¹⁸F]102, and [¹⁸F]F103 according to the present invention each had a radioactivity accumulation decreased over time in tissues (the liver, kidney, and spleen) surrounding the adrenal glands, and high radioactivity accumulation that would be an obstacle in the adrenal gland imaging was not observed.

This application claims the priority based on Japanese Patent Application No. 2017-253837 filed on Dec. 28, 2017, the disclosure of which is incorporated herein by reference in its entirety.

The invention claimed is:

1. A compound represented by the following formula (1):

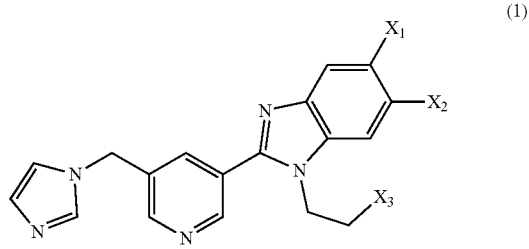

(1)

wherein $X_1$ is a hydrogen atom or a halogen atom, $X_2$ is a fluorine atom or a nitrile group, and $X_3$ represents is a radioactive fluorine atom, or a salt thereof.

2. The compound or a salt thereof according to claim 1, wherein $X_1$ is a hydrogen atom in the formula (1).

3. The compound or a salt thereof according to claim 2, wherein $X_2$ is a fluorine atom in the formula (1).

4. The compound or a salt thereof according to claim 1, wherein $X_1$ is a halogen atom in the formula (1).

5. A medicament, comprising the compound or a salt thereof according to claim 1.

6. The medicament according to claim 5, wherein the medicament is a diagnostic imaging agent for adrenal gland disease.

7. The medicament according to claim 5, wherein the medicament is a diagnostic imaging agent for positron emission tomography.

8. A compound represented by the following formula (2):

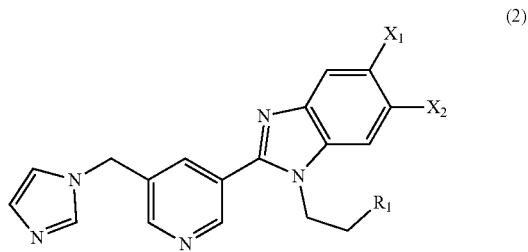

(2)

wherein $X_1$ is a hydrogen atom or a halogen atom, $X_2$ is a fluorine atom or a nitrile group, and $R_1$ is a halogen atom, a substituted or unsubstituted alkylsulfonyloxy group, or a substituted or unsubstituted arylsulfonyloxy group, or a salt thereof.

9. A method for producing a radioactive compound represented by the following formula (1):

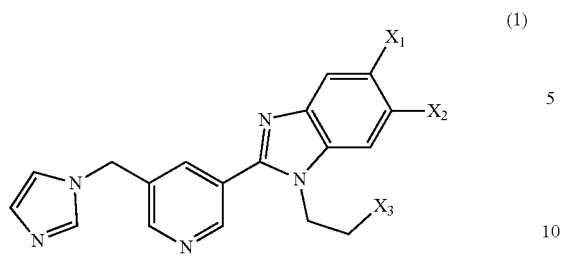
wherein $X_1$ is a hydrogen atom or a halogen atom, $X_2$ is a fluorine atom or a nitrile group, and $X_3$ is a radioactive halogen atom,
or a salt thereof, by a radiohalogenation on reaction from the compound or a salt thereof according to claim 8.
\* \* \* \* \*